US008075872B2

(12) United States Patent
Arkenau-Maric et al.

(10) Patent No.: US 8,075,872 B2
(45) Date of Patent: *Dec. 13, 2011

(54) ABUSE-PROOFED DOSAGE FORM

(75) Inventors: Elisabeth Arkenau-Maric, Köln (DE); Johannes Bartholomäus, Aachen (DE); Heinrich Kugelmann, Aachen (DE)

(73) Assignee: Gruenenthal GmbH, Aachen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 11/349,544

(22) Filed: Feb. 6, 2006

(65) Prior Publication Data

US 2007/0183979 A1    Aug. 9, 2007

Related U.S. Application Data

(63) Continuation-in-part of application No. 10/718,112, filed on Nov. 20, 2003.

(30) Foreign Application Priority Data

Aug. 6, 2003   (DE) .................................. 103 36 400
Feb. 4, 2005   (DE) ........................ 10 2005 005 446

(51) Int. Cl.
*A61K 49/00* (2006.01)

(52) U.S. Cl. ...................................... 424/10.1; 424/10.4

(58) Field of Classification Search ................... 424/10.1
See application file for complete search history.

(56) References Cited

U.S. PATENT DOCUMENTS

| | | | |
|---|---|---|---|
| 3,806,603 A | 4/1974 | Gaunt et al. | |
| 3,865,108 A | 2/1975 | Hartop | |
| 3,966,747 A | 6/1976 | Monkovic | |
| 3,980,766 A | 9/1976 | Shaw et al. | |
| 4,002,173 A | 1/1977 | Manning et al. | |
| 4,014,965 A | 3/1977 | Stube et al. | |
| 4,070,494 A | 1/1978 | Hoffmeister et al. | 424/2 |
| 4,070,497 A | 1/1978 | Wismer et al. | |
| 4,175,119 A * | 11/1979 | Porter | 424/475 |
| 4,207,893 A | 6/1980 | Michaels | |
| 4,262,017 A | 4/1981 | Kuipers et al. | |
| 4,343,789 A | 8/1982 | Kawata et al. | |
| 4,353,887 A | 10/1982 | Hess et al. | |
| 4,404,183 A | 9/1983 | Kawata et al. | |
| 4,427,681 A | 1/1984 | Manshi | |
| 4,462,941 A | 7/1984 | Lee et al. | |
| 4,603,143 A | 7/1986 | Schmidt | |
| 4,612,008 A | 9/1986 | Wong et al. | 604/892 |
| 4,629,621 A | 12/1986 | Snipes | |
| 4,690,822 A | 9/1987 | Uemura et al. | |
| 4,713,243 A | 12/1987 | Schiraldi et al. | |
| 4,744,976 A | 5/1988 | Snipes et al. | |
| 4,764,378 A | 8/1988 | Keith et al. | |
| 4,765,989 A | 8/1988 | Wong et al. | 424/473 |
| 4,774,074 A | 9/1988 | Snipes | |
| 4,783,337 A | 11/1988 | Wong et al. | 424/468 |
| 4,806,337 A | 2/1989 | Snipes et al. | |
| RE33,093 E | 10/1989 | Schiraldi et al. | |
| 4,880,585 A | 11/1989 | Klimesch et al. | |
| 4,892,778 A | 1/1990 | Theeuwes et al. | |
| 4,892,889 A | 1/1990 | Kirk et al. | |
| 4,940,556 A | 7/1990 | MacFarlane et al. | |
| 4,957,668 A | 9/1990 | Placard | |
| 4,957,681 A * | 9/1990 | Klimesch et al. | 264/211.23 |
| 4,960,814 A | 10/1990 | Wu et al. | |
| 4,992,278 A | 2/1991 | Khanna | |
| 4,992,279 A | 2/1991 | Palmer et al. | |
| 5,004,601 A | 4/1991 | Snipes | |
| 5,051,261 A | 9/1991 | McGinity et al. | |
| 5,169,645 A | 12/1992 | Shukla et al. | |
| 5,198,226 A | 3/1993 | MacFarlane et al. | |
| 5,200,197 A | 4/1993 | Wright et al. | |
| 5,211,892 A | 5/1993 | Gueret | |
| 5,273,758 A | 12/1993 | Royce | |
| 5,350,741 A | 9/1994 | Takada | |
| 5,378,462 A | 1/1995 | Boedecker et al. | |
| 5,427,798 A | 6/1995 | Ludwig et al. | |
| RE34,990 E | 7/1995 | Khanna et al. | |
| 5,458,887 A | 10/1995 | Chen et al. | |
| 5,460,826 A | 10/1995 | Merrill et al. | |
| 5,556,640 A | 9/1996 | Ito et al. | |
| 5,562,920 A | 10/1996 | Demmer et al. | |
| 5,601,842 A | 2/1997 | Bartholomaeus | |
| 5,620,697 A | 4/1997 | Tormala et al. | |
| 5,681,517 A | 10/1997 | Metzger | |
| 5,792,474 A | 8/1998 | Rauchfuss | |

(Continued)

FOREIGN PATENT DOCUMENTS

AR   46994   12/2004

(Continued)

OTHER PUBLICATIONS

Zhang et al. (Pharm. Dev. Tech. 1999, 4, 241-250).*

(Continued)

*Primary Examiner* — Michael G Hartley
*Assistant Examiner* — Melissa Perreira
(74) *Attorney, Agent, or Firm* — Norris McLaughlin & Marcus, P.A.

(57) ABSTRACT

The invention relates to a dosage form that is thermoshaped without being extruded and that is safeguarded from abuse, comprising at least one synthetic or natural polymer having a breaking strength of at least 500 N in addition to one or more active substances that could be subject to abuse and optionally physiologically acceptable adjuvants. The invention also relates to a corresponding method for producing said dosage form.

31 Claims, 1 Drawing Sheet

U.S. PATENT DOCUMENTS

| | | | |
|---|---|---|---|
| 5,801,201 A | 9/1998 | Graudums et al. | |
| 5,811,126 A | 9/1998 | Krishnamurthy | |
| 5,849,240 A | 12/1998 | Miller | |
| 5,866,164 A * | 2/1999 | Kuczynski et al. | 424/472 |
| 5,916,584 A | 6/1999 | O'Donoghue et al. | |
| 5,928,739 A | 7/1999 | Pophusen et al. | |
| 5,945,125 A | 8/1999 | Kim | |
| 5,948,787 A | 9/1999 | Merrill et al. | |
| 5,968,925 A | 10/1999 | Knidlberger | |
| 6,009,390 A | 12/1999 | Gupta et al. | |
| 6,009,690 A | 1/2000 | Rosenberg et al. | |
| 6,077,538 A | 6/2000 | Merrill et al. | |
| 6,096,339 A | 8/2000 | Ayer et al. | |
| 6,117,453 A | 9/2000 | Seth et al. | |
| 6,133,241 A | 10/2000 | Bok et al. | |
| 6,228,863 B1 | 5/2001 | Palermo et al. | |
| 6,235,825 B1 | 5/2001 | Yoshida et al. | |
| 6,238,697 B1 * | 5/2001 | Kumar et al. | 424/464 |
| 6,245,357 B1 | 6/2001 | Edgren et al. | |
| 6,248,737 B1 | 6/2001 | Buschmann et al. | |
| 6,261,599 B1 | 7/2001 | Oshlack et al. | |
| 6,306,438 B1 | 10/2001 | Oshlack et al. | |
| 6,309,668 B1 | 10/2001 | Bastin et al. | |
| 6,340,475 B2 | 1/2002 | Shell et al. | |
| 6,344,535 B1 | 2/2002 | Timmermann et al. | |
| 6,348,469 B1 | 2/2002 | Seth | |
| 6,375,963 B1 | 4/2002 | Repka et al. | |
| 6,399,100 B1 | 6/2002 | Clancy et al. | |
| 6,419,954 B1 | 7/2002 | Chu et al. | |
| 6,436,441 B1 | 8/2002 | Sako et al. | |
| 6,461,644 B1 | 10/2002 | Jackson et al. | |
| 6,488,962 B1 | 12/2002 | Berner et al. | |
| 6,488,963 B1 | 12/2002 | McGinity et al. | |
| 6,534,089 B1 | 3/2003 | Ayer et al. | |
| 6,547,997 B1 * | 4/2003 | Breitenbach et al. | 264/85 |
| 6,562,375 B1 | 5/2003 | Sako | |
| 6,592,901 B2 | 7/2003 | Durig et al. | |
| 6,635,280 B2 | 10/2003 | Shell et al. | |
| 6,699,503 B1 | 3/2004 | Sako et al. | |
| 6,723,340 B2 | 4/2004 | Gusler et al. | |
| 6,733,783 B2 * | 5/2004 | Oshlack et al. | 424/473 |
| 6,753,009 B2 | 6/2004 | Luber | |
| 6,821,588 B1 | 11/2004 | Hammer et al. | |
| 7,141,250 B2 | 11/2006 | Oshlack et al. | |
| 7,176,251 B1 | 2/2007 | Bastioli et al. | |
| 7,776,314 B2 | 8/2010 | Bartholomäus et al. | |
| 2001/0038852 A1 | 11/2001 | Kolter et al. | |
| 2002/0001270 A1 | 1/2002 | Fukuchi et al. | |
| 2002/0005182 A1 | 1/2002 | Kraus et al. | |
| 2002/0011483 A1 | 1/2002 | Kishimoto | |
| 2002/0012701 A1 | 1/2002 | Kolter et al. | |
| 2002/0015730 A1 | 2/2002 | Hoffmann et al. | |
| 2002/0018719 A1 | 2/2002 | Arilla et al. | |
| 2002/0051820 A1 | 5/2002 | Shell | |
| 2002/0114838 A1 | 8/2002 | Ayer et al. | |
| 2002/0132359 A1 | 9/2002 | Waterman | |
| 2002/0187192 A1 | 12/2002 | Joshi et al. | |
| 2003/0010405 A1 | 1/2003 | Clark et al. | |
| 2003/0015814 A1 | 1/2003 | Krull et al. | |
| 2003/0017532 A1 | 1/2003 | Biswas et al. | |
| 2003/0021546 A1 | 1/2003 | Sato | |
| 2003/0031546 A1 | 2/2003 | Araki et al. | |
| 2003/0044458 A1 * | 3/2003 | Wright et al. | 424/458 |
| 2003/0044464 A1 | 3/2003 | Ziegler et al. | |
| 2003/0064099 A1 * | 4/2003 | Oshlack et al. | 424/465 |
| 2003/0068392 A1 | 4/2003 | Sackler | 424/760 |
| 2003/0091630 A1 | 5/2003 | Louie-Helm et al. | |
| 2003/0104052 A1 | 6/2003 | Berner et al. | |
| 2003/0118641 A1 | 6/2003 | Maloney et al. | |
| 2003/0124185 A1 | 7/2003 | Oshlack et al. | 424/465 |
| 2003/0125347 A1 | 7/2003 | Anderson | |
| 2003/0133985 A1 | 7/2003 | Louie-Helm et al. | |
| 2003/0152622 A1 | 8/2003 | Louie-Helm et al. | |
| 2003/0158242 A1 | 8/2003 | Kugelmann | |
| 2003/0175326 A1 | 9/2003 | Thombre | |
| 2003/0232895 A1 | 12/2003 | Omidian et al. | |
| 2004/0010000 A1 | 1/2004 | Ayer et al. | |
| 2004/0011806 A1 | 1/2004 | Luciano et al. | |
| 2004/0052844 A1 | 3/2004 | Hsiao et al. | |
| 2004/0081694 A1 | 4/2004 | Oshlack et al. | |
| 2004/0091528 A1 | 5/2004 | Rogers et al. | |
| 2004/0131671 A1 | 7/2004 | Zhang et al. | |
| 2004/0156899 A1 | 8/2004 | Louie-Helm et al. | |
| 2004/0170567 A1 * | 9/2004 | Sackler | 424/10.1 |
| 2004/0185105 A1 | 9/2004 | Berner et al. | |
| 2004/0213848 A1 | 10/2004 | Li et al. | |
| 2005/0015730 A1 | 1/2005 | Gunturi et al. | |
| 2005/0031546 A1 | 2/2005 | Bartholomaus et al. | |
| 2005/0058706 A1 | 3/2005 | Bartholomaeus et al. | |
| 2005/0063214 A1 | 3/2005 | Takashima | |
| 2005/0089475 A1 | 4/2005 | Gruber | |
| 2005/0095291 A1 | 5/2005 | Oshlack et al. | |
| 2005/0106249 A1 | 5/2005 | Hwang et al. | |
| 2005/0112067 A1 | 5/2005 | Kumar et al. | |
| 2005/0127555 A1 | 6/2005 | Gusik et al. | |
| 2005/0152843 A1 | 7/2005 | Bartholomaus et al. | |
| 2005/0186139 A1 | 8/2005 | Bartholomaus et al. | |
| 2005/0191244 A1 | 9/2005 | Bartholomaus et al. | |
| 2005/0214223 A1 | 9/2005 | Bartholomaeus et al. | |
| 2005/0236741 A1 | 10/2005 | Arkenau et al. | |
| 2005/0266084 A1 | 12/2005 | Li et al. | |
| 2006/0002859 A1 | 1/2006 | Arkenau et al. | |
| 2006/0002860 A1 | 1/2006 | Bartholomaus et al. | |
| 2006/0039864 A1 | 2/2006 | Bartholomaus et al. | |
| 2006/0099250 A1 | 5/2006 | Tian et al. | |
| 2006/0188447 A1 | 8/2006 | Arkenau-Maric et al. | |
| 2006/0193782 A1 | 8/2006 | Bartholomaus et al. | |
| 2006/0193914 A1 | 8/2006 | Ashworth et al. | |
| 2006/0240110 A1 | 10/2006 | Kiick et al. | |
| 2007/0003616 A1 | 1/2007 | Arkenau-Maric et al. | |
| 2007/0020188 A1 | 1/2007 | Sackler | |
| 2007/0020335 A1 | 1/2007 | Chen et al. | |
| 2007/0048228 A1 | 3/2007 | Arkenau-Maric et al. | |
| 2007/0065365 A1 | 3/2007 | Kugelmann et al. | |
| 2007/0092573 A1 | 4/2007 | Joshi et al. | |
| 2007/0183979 A1 | 8/2007 | Arkenau-Maric et al. | |
| 2007/0183980 A1 | 8/2007 | Arkenau-Maric et al. | |
| 2007/0190142 A1 | 8/2007 | Breitenbach et al. | |
| 2007/0196396 A1 | 8/2007 | Pilgaonkar et al. | |
| 2007/0196481 A1 | 8/2007 | Amidon et al. | |
| 2007/0264327 A1 | 11/2007 | Kumar et al. | |
| 2007/0269505 A1 | 11/2007 | Flath | |
| 2008/0081290 A1 | 4/2008 | Wada et al. | |
| 2008/0247959 A1 | 10/2008 | Bartholomaus et al. | |
| 2008/0248113 A1 | 10/2008 | Bartholomaus et al. | |
| 2008/0311049 A1 | 12/2008 | Bartholomaus et al. | |
| 2008/0311187 A1 | 12/2008 | Ashworth et al. | |
| 2008/0311197 A1 | 12/2008 | Arkenau-Maric et al. | |
| 2008/0312264 A1 | 12/2008 | Arkenau-Maric et al. | |
| 2008/0317854 A1 | 12/2008 | Arkenau et al. | |
| 2009/0004267 A1 | 1/2009 | Arkenau-Maric et al. | |
| 2009/0005408 A1 | 1/2009 | Arkenau-Maric et al. | |
| 2009/0081290 A1 | 3/2009 | McKenna et al. | |
| 2009/0202634 A1 | 8/2009 | Jans et al. | |
| 2010/0015223 A1 | 1/2010 | Cailly-Dufestel et al. | |
| 2010/0098758 A1 | 4/2010 | Bartholomaus et al. | |
| 2010/0151028 A1 | 6/2010 | Ashworth et al. | |
| 2010/0221322 A1 | 9/2010 | Bartholomaus et al. | |
| 2010/0260833 A1 | 10/2010 | Bartholomaus et al. | |
| 2011/0020451 A1 | 1/2011 | Bartholomaus et al. | |
| 2011/0038930 A1 | 2/2011 | Barnscheid et al. | |
| 2011/0082214 A1 | 4/2011 | Fauer et al. | |

FOREIGN PATENT DOCUMENTS

| | | |
|---|---|---|
| AR | 045353 | 10/2005 |
| AR | 049562 | 8/2006 |
| AR | 053304 | 5/2007 |
| AR | 054222 | 6/2007 |
| AR | 054328 | 6/2007 |
| AU | 2003237944 | 12/2003 |
| AU | 2003274071 | 5/2004 |
| AU | 2003278133 | 5/2004 |
| AU | 2003279317 | 5/2004 |
| AU | 2004264666 | 2/2005 |
| AU | 2004264667 | 2/2005 |
| AU | 2004308653 | 4/2005 |
| AU | 2005259476 | 1/2006 |

| | | | | | |
|---|---|---|---|---|---|
| AU | 2005259478 | 1/2006 | EP | 0598606 | 5/1994 |
| AU | 2006210145 | 8/2006 | EP | 0636370 | 2/1995 |
| AU | 2009207796 | 7/2009 | EP | 0 641 195 | 3/1995 |
| AU | 2009243681 | 11/2009 | EP | 0647448 | 4/1995 |
| BR | PI0413318 | 10/2006 | EP | 0661045 | 7/1995 |
| BR | PI0413361 | 10/2006 | EP | 0675710 | 10/1995 |
| BR | PI0513300 | 5/2008 | EP | 0682945 | 11/1995 |
| BR | PI0606145 | 2/2009 | EP | 0682945 A2 | 11/1995 |
| CA | 2317747 | 7/1999 | EP | 0 693 475 | 1/1996 |
| CA | 2352874 | 11/1999 | EP | 0820693 | 1/1996 |
| CA | 2502965 | 5/2004 | EP | 0696598 | 2/1996 |
| CA | 2534925 | 2/2005 | EP | 0216453 | 3/1996 |
| CA | 2534932 | 2/2005 | EP | 0756480 | 2/1997 |
| CA | 2551231 | 7/2005 | EP | 0760654 | 3/1997 |
| CA | 2572352 | 1/2006 | EP | 0 780 369 | 6/1997 |
| CA | 2572491 | 1/2006 | EP | 0 820 698 | 7/1997 |
| CA | 2595954 | 7/2006 | EP | 0785775 | 7/1997 |
| CA | 2595979 | 8/2006 | EP | 0809488 | 12/1997 |
| CA | 2713128 | 7/2009 | EP | 0857062 | 8/1998 |
| CA | 2723438 | 11/2009 | EP | 0864324 | 9/1998 |
| CH | 689109 | 10/1998 | EP | 0864326 | 9/1998 |
| CN | 1980643 | 4/2005 | EP | 0 980 894 A1 | 9/1999 |
| CN | 101010071 | 6/2005 | EP | 0988106 | 3/2000 |
| CN | 101022787 | 1/2006 | EP | 1014941 | 7/2000 |
| CN | 001863513 | 11/2006 | EP | 1070504 | 1/2001 |
| CN | 001863514 | 11/2006 | EP | 1127871 | 8/2001 |
| CN | 01917862 | 2/2007 | EP | 1138321 | 10/2001 |
| CN | 101027044 | 8/2007 | EP | 1166776 | 1/2002 |
| CN | 101111232 | 1/2008 | EP | 1251120 | 10/2002 |
| CN | 101175482 | 2/2008 | EP | 1293127 A2 | 3/2003 |
| DE | 2530563 | 1/1977 | EP | 1293196 | 3/2003 |
| DE | 2808505 | 9/1978 | EP | 1250045 B1 | 9/2003 |
| DE | 4309528 A1 | 9/1994 | EP | 1658055 | 2/2005 |
| DE | 69400215 T2 | 10/1996 | EP | 1515702 | 3/2005 |
| DE | 195 22 899 | 12/1996 | EP | 1527775 | 4/2005 |
| DE | 198 22 979 | 2/1999 | EP | 1558221 A1 | 8/2005 |
| DE | 197 53 534 | 6/1999 | EP | 1558257 | 8/2005 |
| DE | 198 00 698 | 7/1999 | EP | 1560585 | 8/2005 |
| DE | 19800689 C1 | 7/1999 | EP | 1658054 | 5/2006 |
| DE | 69229881 | 12/1999 | EP | 1740161 | 1/2007 |
| DE | 19855440 A1 | 6/2000 | EP | 1765303 | 3/2007 |
| DE | 19856147 | 6/2000 | EP | 1786403 | 5/2007 |
| DE | 19940740 | 3/2001 | EP | 1558221 B1 | 6/2007 |
| DE | 19960494 A1 | 6/2001 | EP | 1845955 | 10/2007 |
| DE | 10036400 | 6/2002 | EP | 1845956 | 10/2007 |
| DE | 10036400 A1 | 6/2002 | EP | 1859789 | 11/2007 |
| DE | 69429710 T2 | 8/2002 | EP | 2131830 | 12/2009 |
| DE | 10250083 A1 | 12/2003 | EP | 1897545 | 1/2010 |
| DE | 10250084 A1 | 5/2004 | EP | 2192457 | 6/2010 |
| DE | 10250087 | 5/2004 | EP | 2249811 | 11/2010 |
| DE | 10250088 | 5/2004 | EP | 2273983 | 1/2011 |
| DE | 10336400 A1 | 3/2005 | ES | 2336571 | 12/2004 |
| DE | 102004019916 | 11/2005 | ES | 2260042 | 11/2006 |
| DE | 102004020220 | 11/2005 | ES | 2285497 | 11/2007 |
| DE | 10 2004 032049 | 1/2006 | ES | 2288621 | 1/2008 |
| DE | 10 2004 032051 | 1/2006 | ES | 2289542 | 2/2008 |
| DE | 10 2004 032103 | 1/2006 | ES | 2315505 | 4/2009 |
| DE | 10 2005 005446 | 8/2006 | GB | 1 147 210 | 4/1969 |
| DE | 10 2005 005449 | 8/2006 | GB | 2057878 | 4/1981 |
| DE | 102007011485 | 9/2008 | HR | P20070272 | 6/2007 |
| DK | 1658055 | 7/2007 | HR | 20070456 | 11/2007 |
| DK | 1658054 | 10/2007 | JP | 8 505076 | 6/1996 |
| DK | 1515702 | 1/2009 | JP | 2002-275175 | 9/2002 |
| EC | SP066345 | 8/2006 | JP | 2005534664 | 11/2005 |
| EP | 0 043 254 A1 | 6/1982 | KR | 1020060069832 | 6/2006 |
| EP | 0008131 | 12/1982 | KR | 20070039041 | 4/2007 |
| EP | 0177893 | 4/1986 | KR | 20070111510 | 11/2007 |
| EP | 0 229 652 A2 | 7/1987 | KR | 20100111303 | 10/2010 |
| EP | 0232877 | 8/1987 | KR | 20110016921 | 2/2011 |
| EP | 0 261 616 A2 | 3/1988 | MX | 2007000008 | 3/2007 |
| EP | 0270954 | 6/1988 | MX | 2007000009 | 3/2007 |
| EP | 0277289 | 8/1988 | MX | 2007009393 | 8/2007 |
| EP | 0293066 | 11/1988 | MX | 2010008138 | 8/2010 |
| EP | 0328775 | 8/1989 | MX | 2010012039 | 11/2010 |
| EP | 0228417 | 8/1990 | NO | 20061054 | 3/2006 |
| EP | 0 477 135 A1 | 3/1992 | NO | 20070578 | 1/2007 |
| EP | 0544144 | 6/1993 | NO | 20074412 | 11/2007 |
| EP | 0226061 | 2/1994 | PT | 1699440 | 12/2004 |
| EP | 0583726 | 2/1994 | PT | 1658054 | 5/2006 |

| | | |
|---|---|---|
| PT | 1658055 | 7/2007 |
| PT | 1515702 | 12/2008 |
| RU | 2131244 | 6/1999 |
| RU | 2354357 | 12/2007 |
| RU | 2007103712 | 9/2008 |
| RU | 2007103707 | 11/2008 |
| RU | 2007132975 | 4/2009 |
| SI | 1515702 | 4/2009 |
| SI | 1699440 | 11/2009 |
| WO | 89/05624 | 6/1989 |
| WO | 90/03776 | 4/1990 |
| WO | 90 03776 | 4/1990 |
| WO | 93 06723 | 4/1993 |
| WO | 93/10758 | 6/1993 |
| WO | 93/11749 | 6/1993 |
| WO | 94/06414 | 3/1994 |
| WO | 94/08567 | 4/1994 |
| WO | 95 17174 A1 | 6/1995 |
| WO | 95/22319 | 8/1995 |
| WO | WO 95/20947 | 8/1995 |
| WO | 95/30422 | 11/1995 |
| WO | 96/00066 | 1/1996 |
| WO | 96 03979 A1 | 2/1996 |
| WO | 96/14058 | 5/1996 |
| WO | 9733566 | 9/1997 |
| WO | 9820073 | 5/1998 |
| WO | WO 98/20073 | 5/1998 |
| WO | 98/28698 | 7/1998 |
| WO | 98 35655 A2 | 8/1998 |
| WO | 99 12864 A1 | 3/1999 |
| WO | 99/32120 | 7/1999 |
| WO | 99/48481 | 9/1999 |
| WO | 9944591 A1 | 9/1999 |
| WO | WO0033835 * | 6/2000 |
| WO | 0040205 | 7/2000 |
| WO | 01/12230 | 2/2001 |
| WO | 0108661 A2 | 2/2001 |
| WO | 0115667 A1 | 3/2001 |
| WO | 01/52651 | 7/2001 |
| WO | 01/97783 | 12/2001 |
| WO | 02/26061 | 4/2002 |
| WO | 02/26262 | 4/2002 |
| WO | 02/26928 | 4/2002 |
| WO | 02/088217 | 11/2002 |
| WO | 03/001476 | 1/2003 |
| WO | 03/006723 | 1/2003 |
| WO | 03/013476 | 2/2003 |
| WO | 03/013479 | 2/2003 |
| WO | WO 03/015531 A2 | 2/2003 |
| WO | 03 024430 | 3/2003 |
| WO | 03/026624 | 4/2003 |
| WO | 03 028698 | 4/2003 |
| WO | 03/028990 | 4/2003 |
| WO | 03/031546 | 4/2003 |
| WO | 2003 026743 A2 | 4/2003 |
| WO | 03/035177 | 5/2003 |
| WO | 03035029 A1 | 5/2003 |
| WO | 03035053 A1 | 5/2003 |
| WO | 03035054 A1 | 5/2003 |
| WO | 03053417 A2 | 7/2003 |
| WO | 03/068392 | 8/2003 |
| WO | 03/092648 | 11/2003 |
| WO | 03094812 A1 | 11/2003 |
| WO | 03/105808 | 12/2003 |
| WO | 2004 004693 A1 | 1/2004 |
| WO | 2004/011806 | 2/2004 |
| WO | 2004/026263 | 4/2004 |
| WO | 2004026262 A2 | 4/2004 |
| WO | 2004/043967 | 5/2004 |
| WO | 2004037230 A1 | 5/2004 |
| WO | 2004037259 A1 | 5/2004 |
| WO | 2004037260 A1 | 5/2004 |
| WO | 2004/066910 | 8/2004 |
| WO | 2004/084869 | 10/2004 |
| WO | 2004/093801 | 11/2004 |
| WO | 2004/100894 | 11/2004 |
| WO | 2004093819 A2 | 11/2004 |
| WO | 2005 016313 | 2/2005 |
| WO | 2005/032524 | 4/2005 |
| WO | 2005/041968 | 5/2005 |
| WO | 2005 053656 A1 | 6/2005 |
| WO | 2005/065646 | 7/2005 |
| WO | 2005/066183 | 7/2005 |
| WO | 2005016314 A1 | 7/2005 |
| WO | 2005063214 A1 | 7/2005 |
| WO | 2005102286 A1 | 11/2005 |
| WO | 2005102294 | 11/2005 |
| WO | 2006/002883 | 1/2006 |
| WO | 2006/002884 | 1/2006 |
| WO | 2006/002886 | 1/2006 |
| WO | 2006002884 | 1/2006 |
| WO | 2006/082097 | 8/2006 |
| WO | 2006/082099 | 8/2006 |
| WO | 2007/005716 | 1/2007 |
| WO | 2007/008752 | 1/2007 |
| WO | 2007/048233 | 5/2007 |
| WO | 2007/053698 | 5/2007 |
| WO | 2007/085024 | 7/2007 |
| WO | 2008 086804 A2 | 7/2008 |
| WO | 2008 107149 A2 | 9/2008 |
| WO | 2008107149 | 9/2008 |
| WO | 2008 148798 A2 | 12/2008 |
| WO | 2009/092601 | 7/2009 |
| WO | 2009092601 | 7/2009 |
| WO | 2009/135680 | 11/2009 |
| WO | 2009135680 | 11/2009 |
| WO | 2011009602 | 1/2011 |
| WO | 2011009603 | 1/2011 |
| WO | 2011009604 | 1/2011 |

OTHER PUBLICATIONS

Maggi et al. (Biomaterials 2002, 23, 1113-1119).*
Dow Polyox data sheet.*
Inert gas—Wikipedia.*
DeJong (Pharmaceutisch Weekblad Scientific Edition 1987, p. 24-28).*
"Coated Pharmaceutical Dosage Forms, Fundamentals, Manufacturing Techniques, Biopharmaceutical Aspects, Test Methods and Raw Materials", Kurt H. Bauer, Ph. D., et al., 1998, Preface, Table of Contents, List of Abbreviations, and Explanation of Terms.
"Pharmaceutical technical procedures", European Pharmacopofia, 1997, p. 135.
Yang, et al; "Characterization of Compressibility and Compactibility of Poly(ethylene oxide) Polymers for Modified Release Application by Compaction Simulator"; Journal of Pharmaceutical Sciences, vol. 85, No. 10, Oct. 1996.
Coppens et al; "Hypromellose, Ethylcellulose, and Polyethylene Oxide Use in Hot Melt Extrusion"; Pharmaceutical Technology, 62-70, Jan. 2005.
Maggi et al, Biomaterials 2002, 23, pp. 1113-1119.
Proeschel et al; J. Dent. Res., 81(7), 2002, pp. 464-468.
Schroder,J., Granulierung hydrophober Wirkstoffe, vol. 65, No. 4, 2003, pp. 367-372.
Stafford, "Uberzogene feste formen"1991, pp. 347-368.
1.2 Klassifizierung von extrudern, pp. 3-7.
Scharfstoffdrogen, Pharmazeutische Biologie Drogen and ihre 1982, pp. 82-92.
2.9 Methoden der pharmazeutische 1997, pp. 143-144.
Remington's Pharmaceutical Sciences, Authur Asol editor, pp. 1553-1593, Chapter 89, 1980.
"Polyox Water-Soluble Resins NF in Pharmaceutical Applications", published by The Dow Chemical Company in Aug. 2004.
Maggi, "Therapeutic Potential of Capsaicin-like Molecules: Studies in Animals and Humans", Life Sciences, vol. 51, pp. 1777-1781, (1992).
Adel El-Egakey et al, Pharmcerutica Acta Helvetiae, vol. 46, Mar. 19, 1970.
Apicella A., Biomaterials, vol. 14, No. 2, pp. 83-90, 1993.
Bailey F.E., Journal of Applied Polymer Science, vol. 1, Issue No. 1, pp. 56-62, 1959.
Braun, et al. Angel Orthodontist, 6(5) pp. 373-377, 1995.
Bauer, et al, Lehrbuch der Pharmazeutischen Technologie, 1999.
Crowley M.M., Biomaterials 23, 2002, pp. 4241-4248.
Caraballo, Journal of Controlled Release, vol. 69, pp. 345-355, 2000.

Davis, et al; European Journal of Pharmaceutics and Biopharmaceutics, 67, 2007, pp. 268-276.
Efentakis M.,Pharmaceutical Development and Technology, 5 (3), pp. 339-346, 2000.
El-Sherbiny, European Polymer Journal, vol. 41, pp. 2584-2591, 2005.
Follonier N., Drug Development and Industrial Pharmacy, 20(8), pp. 1323-1339, 1994.
Follonier N., Journal of Controlled Release 36, pp. 243-250, 1995.
Fell, et al, Journal of Pharmaceutical Sciences, vol. 59, No. 5, May 1970, pp. 688-691.
Graham N.B., Poly(Ethylene Glycol) Chemistry: Biotechnical and Biomedical Applications, Chapter 17, 1992.
Griffith, Drug Administration, vol. 19, No. 1, pp. 41-42, 2003.
Hanning C.D., British Journal of Anaesthesia, 61, pp. 221-227, 1988.
Janicki S., Acta Pharm. Technol. 33 (3) 154-155, 1987.
Kim C.-J. J Pharm. Sciences 1995, 84(3), p. 303-306.
Kim, Chem. Pharm Bull. 1992, 40(10), 2800-2804.
Letter of J.W. McGinity, Jan. 26, 2009.
Levina, Journal of Pharmaceutical Sciences, vol. 89, No. 6, pp. 703-723, Jun. 2000.
Levina, Drug Development and Industrial Pharmacy, vol. 28, No. 5, pp. 495-514, 2002.
Lockhart et al, "Packaging of Pharmaceuticals and Health Care Products"; Blackie Academic & Professional; First Edition 1996.
Madorsky S.L., Journal of Polymer Science, vol. 84, No. 3, Mar. 1959.
Mank R., Pharmazie 44, H. 11, pp. 773-776, 1989.
Mank R., Pharmazie 45, H. 8, pp. 592-593 1990.
Mesiha M.S., Drug Development and Industrial Pharmacy, 19(8), pp. 943-959, 1993.
Moroni A., Drug Development and Industrial Pharmacy, 21(12) pp. 1411-1428, 1995.
Miller, Nursing, pp. 50-52, Feb. 2000.
Mitchell, Special Resource, vol. 35, No. 5, pp. 535-557, 2000.
Manthena et al, Am. J. Drug Deliv. 2004: 2 (1): 43-57.
Ohnishi N., Chem. Pharm. Bull, 35(8), pp. 3511-3515, 1987.
Ozeki T., Journal of Controlled Release 58, pp. 87-95, 1999.
Pharm. Research, 1989, 6(9), 6-98.
Pharm. Research, 1991, 8(10), 8-192.
Radko S., Applied ad Theoretical Electrophoresis 5, pp. 79-88, 1995.
Remington's Pharmaceutical Sciences 17th ed., 1418 (1985).
Rippie E.G., Journal of Pharmaceutical Sciences, Vo. 58, No. 4, pp. 428-431, Apr. 1969.
Sprockel O.L., J. Pharma. Pharmacol. 42, pp. 152-157, 1990.
Stringer J.L., Journal of Controlled Release 42, pp. 195-202, 1996.
Summers et al; Journal of Pharmaceutical Sciences, vol. 66, No. 8, Aug. 1977, pp. 1172-1175.
Thoma V.K., Pharm. Ind. 51, Nr. 3, 1989.
Tipler, et al, Physics for Scientists and Engineers, 6th Edition, pp. 234-235, 2003.
US Pharmacopoeia, Chapter 1217, Aug. 1, 2008.

Yarbrough et al, Letters to Nature 322, 347-349 (Jul. 24, 1986) "Extraordinary effects of mortar-and-pestle grinding on microstructure of sintered alumina gel".
Zhang et al., Pharmaceutical Development and Technology, 1999, 4, 241-250.
Yarbrough et al, Letters to Nature 322, 347-349 (Jul. 24, 1986) Extraordinary effects of mortar-and-pestle grinding on microstructure of sintered alumina ge.
Seach result conducted on http://www.unitconversion.org/force/newtons-to-kiloponds-conversion.html on Jul. 5, 2011.
Prapaitrakul W., J. Pharm. Pharmacol. 43, pp. 377-381, 1991.
Dachille, F. et al., "High-Pressure Phase Transformation in Laboratory Mechanical Mixers and Mortars", 1906., Nature, 186, pp. 1-2 (abstract).
Arnold, "Teen Abuse of Painkiller OxyContin on the Rise," www.npr.org, Dec. 19, 2005.
Baum et al., Public Health Reports, 102(4): 426-429 (1987).
Katz, et al, "Challenges in the Development of Prescription Opioid Abuse-deterrent Formulations", Clin J Pain, Clin J Pain, vol. 23, No. 8, Oct. 2007 : 648-660.
Waltimo, et al, "A novel bite force recorder and maximal isometric bite force values for healthy young adults", Scandinavian Journal of Dental Research 1993; 101: 171-5.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002.
Strang, British Med. J., 302: 969 (Apr. 20, 1991).
Tompkins et al., "Human abuse liability assessment of oxycodone combined with ultra-low-dose naltrexone", Psychopharma., 210: 471-480 (2010).
Waters et al., Am. J. Psychiatry, 164(1): pp. 173-174 (Jan. 2007).
Tablet, www.docstoc.com (2011).
Waltimo, et al, "Maximal bite force and its association with signs and symptoms of craniomandibular disorders in young Finnish non-patients", Acta Odontol Scand 53 (1995) : 254-258.
Maggi, L. et al., "High molecular weight polyethylene oxides (PEOs) as an alternative to HPMC in controlled release dosage form", 2000, International Journal of Pharmaceutics, 195 pp, 229-238.
Scheirs J., "Characterizing the Solid-State Thermal Oxidation of Poly (ethylene oxide) Powder", Polymer, vol. 32, No. 11, 1991.
Jan. 6, 2011 Letter from Dr. Rick Matos, Ph.D.
Freed et al., "pH Control of Nucleophilic/electrophilic oxidation", International Journal of Pharmaceutics, vol. 357, pp. 180-188, (2008).
Waterman et al., "Stabilization of Pharmaceuticals to Oxidative Degradation", Pharmaceutical Development and Technology, vol. 7(1), pp. 1-32, (2002).

* cited by examiner

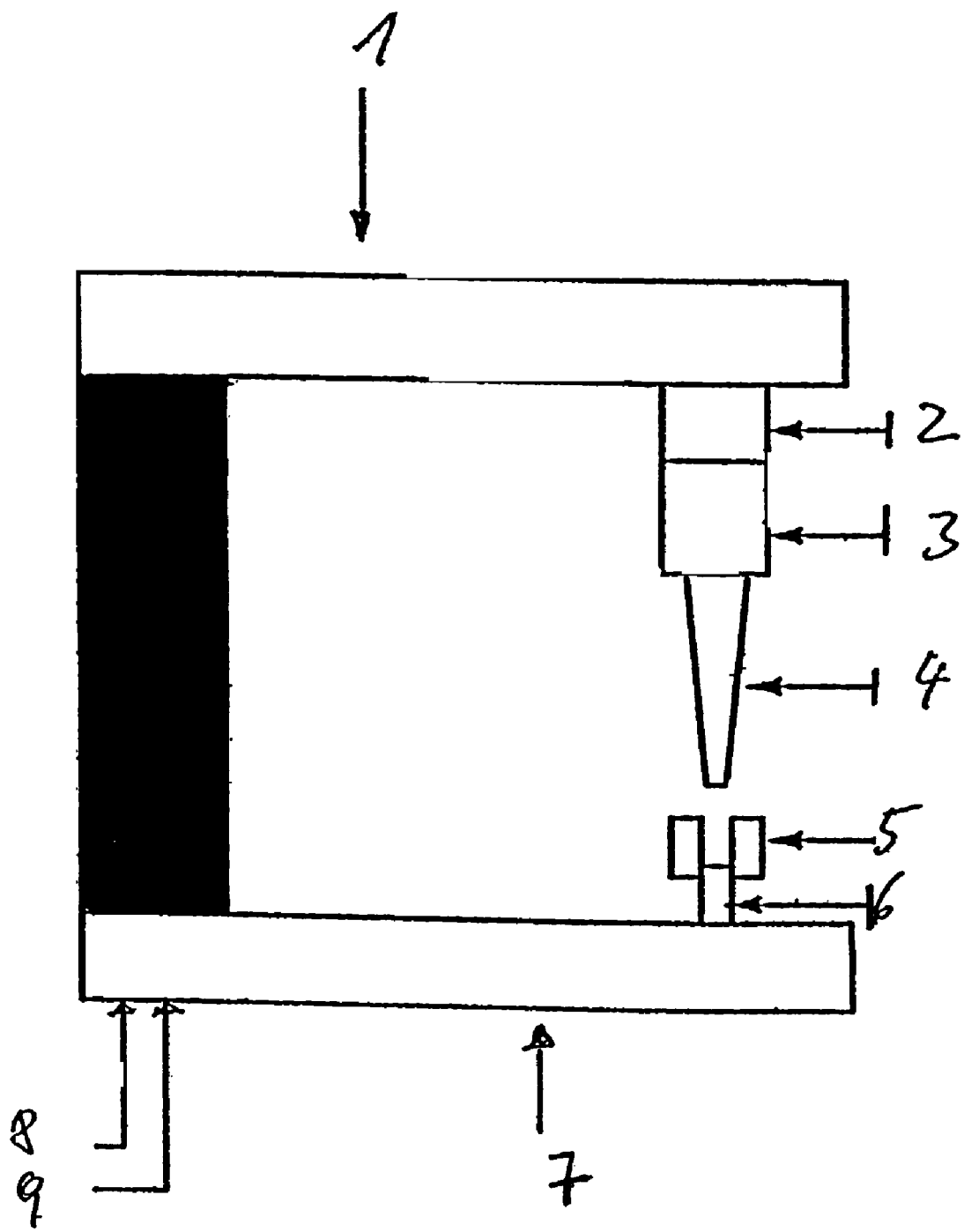

ABUSE-PROOFED DOSAGE FORM

CROSS-REFERENCE TO RELATED APPLICATIONS

This application is a Continuation-in-Part-Application of pending U.S. patent application Ser. No. 10/718,112 filed on Nov. 20, 2003 and claims priority of German Patent Application No. 10 2005 005446.3 filed on Feb. 4, 2005 and German Patent Application No. 10 336 400.5 filed on Aug. 6, 2003.

The present invention relates to an abuse-proofed dosage form thermoformed by extrusion without discoloration and containing, in addition to one or more active ingredients with abuse potential (A) optionally together with physiologically acceptable auxiliary substances (B), at least one synthetic or natural polymer (C) and optionally at least one wax (D), wherein component (C) and the optionally present component (D) each exhibit a breaking strength of at least 500 N, and to a process for the production of the dosage form according to the invention.

Many pharmaceutical active ingredients, in addition to having excellent activity in their appropriate application, also have abuse potential, i.e. they can be used by an abuser to bring about effects other than those intended. Opiates, for example, which are highly active in combating severe to very severe pain, are frequently used by abusers to induce a state of narcosis or euphoria.

In order to make abuse possible, the corresponding dosage forms, such as tablets or capsules are comminuted, for example ground in a mortar, by the abuser, the active ingredient is extracted from the resultant powder using a preferably aqueous liquid and the resultant solution, optionally after being filtered through cotton wool or cellulose wadding, is administered parenterally, in particular intravenously. An additional phenomenon of this kind of administration, in comparison with abusive oral administration, is a further accelerated increase in active ingredient levels giving the abuser the desired effect, namely the "kick" or "rush". This kick is also obtained if the powdered dosage form is administered nasally, i.e. is sniffed. Since controlled-release dosage forms containing active ingredients with abuse potential do not give rise to the kick desired by the abuser when taken orally even in abusively high quantities, such dosage forms are also comminuted and extracted in order to be abused.

U.S. Pat. No. 4,070,494 proposed adding a swellable agent to the dosage form in order to prevent abuse. When water is added to extract the active ingredient, this agent swells and ensures that the filtrate separated from the gel contains only a small quantity of active ingredient.

The multilayer tablet disclosed in WO 95/20947 is based on a similar approach to preventing parenteral abuse, said tablet containing the active ingredient with abuse potential and at least one gel former, each in different layers.

WO 03/015531 A2 discloses another approach to preventing parenteral abuse. A dosage form containing an analgesic opioid and a dye as an aversive agent is described therein. The colour released by tampering with the dosage form is intended to discourage the abuser from using the dosage form which has been tampered with.

Another known option for complicating abuse involves adding antagonists to the active ingredients to the dosage form, for example naloxone or naltexone in the case of opioids, or compounds which cause a physiological defence response, such as for example ipecacuanha (ipecac) root.

However, since in most cases of abuse it is still necessary to pulverise the dosage form comprising an active ingredient suitable for abuse, it was the object of the present invention to complicate or prevent the pulverisation preceding abuse of the dosage form using the means conventionally available to a potential abuser and accordingly to provide a dosage form for active ingredients with potential for abuse which ensures the desired therapeutic effect when correctly administered, but from which the active ingredients cannot be converted into a form suitable for abuse simply by pulverisation.

Said object has been achieved by the provision of the abuse-proofed dosage form thermoformed by extrusion without discoloration according to the invention which contains, in addition to one or more active ingredients with abuse potential (A), at least one synthetic or natural polymer (C) and optionally at least one wax (D), wherein component (C) and the optionally present component (D) each exhibit a breaking strength of at least 500 N.

The use of polymers having the stated minimum breaking strength (measured as stated in the application), preferably in quantities such that the dosage form also exhibits such a minimum breaking strength of at least 500 N, means that pulverisation of the dosage form is considerably more difficult using conventional means, so considerably complicating or preventing the subsequent abuse.

If comminution is inadequate, parenteral, in particular intravenous, administration cannot be performed safely or extraction of the active ingredient therefrom takes too long for the abuser or there is no "kick" when taken orally, as release is not instantaneous.

According to the invention, comminution is taken to mean pulverisation of the dosage form with conventional means which are available to an abuser, such as for example a mortar and pestle, a hammer, a mallet or other usual means for pulverisation by application of force.

The dosage form according to the invention is thus suitable for preventing parenteral, nasal and/or oral abuse of active ingredients, preferably of pharmaceutical active ingredients, with abuse potential.

Pharmaceutical active ingredients with abuse potential are known to the person skilled in the art, as are the quantities thereof to be used and processes for the production thereof, and may be present in the dosage form according to the invention as such, in the form of the corresponding derivatives thereof, in particular esters or ethers, or in each case in the form of corresponding physiologically acceptable compounds, in particular in the form of the salts or solvates thereof, as racemates or stereoisomers. The dosage form according to the invention is also suitable for the administration of two or more pharmaceutical active ingredients in one dosage form. The dosage form preferably contains just one specific active ingredient.

The dosage form according to the invention is in particular suitable for preventing abuse of a pharmaceutical active ingredient selected from the group consisting of opioids, tranquillisers, preferably benzodiazepines, barbiturates, stimulants and other narcotics.

The dosage form according to the invention is very particularly suitable for preventing abuse of an opioid, tranquilliser or another narcotic selected from the group consisting of N-{1-[2-(4-ethyl-5-oxo-2-tetrazolin-1-yl) ethyl]-4-methoxymethyl-4-piperidyl} propionanilide (alfentanil), 5,5-diallylbarbituric acid (allobarbital), allylprodine, alphaprodine, 8-chloro-1-methyl-6-phenyl-4H-[1,2,4] triazolo [4,3-a][1,4]-benzodiazepine (alprazolam), 2-diethylaminopropiophenone (amfepramone), (±)-a-methyl-phenethylamine (amphetamine), 2-(a-methylphenethylamino)-2-phenylacetonitrile (amphetaminil), 5-ethyl-5-isopentylbarbituric acid (amobarbital), anileridine, apocodeine, 5,5-diethylbarbituric acid (barbital), benzylmorphine, bezitramide, 7-bromo-5-(2- pyridyl)-1H-1,4-benzodiazepine-2(3H)-one (bromazepam), 2-bromo-4-(2-chlorophenyl)-9-methyl-6H-thieno [3,2-f] [1,2,4] triazolo-[4,3-a] [1,4] diazepine (brotizolam), 17-cyclopropylmethyl-4,5a-epoxy-7a [(S)-1-hydroxy-1,2,2-trimethyl-propyl]-6-methoxy-6,14-endo-ethanomorphinan-3-ol (buprenorphine), 5-butyl-5-ethylbarbituric acid (butobarbital), butorphanol, (7-chloro-1,3-dihydro-1-methyl-2-oxo-5-phenyl-2H-1,4-benzodiazepin-3-yl) dimethylcarbamate (camazepam), (1S,2S)-2-amino-1-phenyl-1-propanol (cathine/D-norpseudoephedrine), 7-chloro-N-methyl-5-phenyl-3H-1,4-benzodiazepin-2-ylamine 4-oxide (chlordiazepoxide), 7-chloro-1-methyl-5-phenyl-1H-1,5-benzodiazepine-2,4(3H,5H)-dione (clobazam), 5-(2-chlorophenyl)-7-nitro-1H-1,4-benzodiazepin-2(3H)-one (clonazepam), clonitazene, 7-chloro-2,3-dihydro-2-oxo-5-phenyl-1H-1,4-benzodiazepine-3-carboxylic acid (clorazepate), 5-(2-chlorophenyl)-7-ethyl-1-methyl-1H-thieno[2,3-e] [1,4] diazepin-2(3H)-one (clotiazepam), 10-chloro-11b-(2-chlorophenyl)-2,3,7,11b-tetrahydrooxazolo-[3,2-d] [1,4] benzodiazepin-6 (5H)-one (cloxazolam), (−)-methyl-[3β-benzoyloxy-2β (1aH,5aH)-tropancarboxylate] (cocaine), 4,5a-epoxy-3-methoxy-17-methyl-7-morphinan-6a-ol (codeine), 5-(1-cyclohexenyl)-5-ethylbarbituric acid (cyclobarbital), cyclorphan, cyprenorphine, 7-chloro-5-(2-chlorophenyl)-1H-1,4-benzodiazepin-2(3H)-one (delorazepam), desomorphine, dextromoramide, (+)-(1-benzyl-3-dimethylamino-2-methyl-1-phenylpropyl)propionate (dextropropoxyphen), dezocine, diampromide, diamorphone, 7-chloro-1-methyl-5-phenyl-1H-1,4-benzodiazepin-2(3H)-one (diazepam), 4,5a-epoxy-3-methoxy-17-methyl-6a-morphinanol (dihydrocodeine), 4,5α-epoxy-17-methyl-3,6a-morphinandiol (dihydromorphine), dimenoxadol, dimepheptanol, dimethylthiambutene, dioxaphetyl butyrate, dipipanone, (6aR, 10aR)-6,6,9-trimethyl-3-pentyl-6a,7,8,10a-tetrahydro-6H-benzo [c] chromen-1-ol (dronabinol), eptazocine, 8-chloro-6-phenyl-4H-[1,2,4] triazolo[4,3-a] [1,4] benzodiazepine (estazolam), ethoheptazine, ethylmethylthiambutene, ethyl [7-chloro-5-(2-fluorophenyl)-2,3-dihydro-2-oxo-1H-1,4-benzodiazepine-3-carboxylate] (ethyl loflazepate), 4,5α-epoxy-3-ethoxy-17-methyl-7-morphinen-6α-ol (ethylmorphine), etonitazene, 4,5α-epoxy-7α-(1-hydroxy-1-methylbutyl)-6-methoxy-17-methyl-6,14-endo-etheno-morphinan-3-ol (etorphine), N-ethyl-3-phenyl-8,9,10-trinorbornan-2-ylamine (fencamfamine), 7-[2-(α-methyl-phenethylamino) ethyl]-theophylline (fenethylline), 3-(α-methylphenethylamino) propionitrile (fenproporex), N-(1-phenethyl-4-piperidyl) propionanilide (fentanyl), 7-chloro-5-(2-fluorophenyl)-1-methyl-1H-1,4-benzodiazepin-2(3H)-one (fludiazepam), 5-(2-fluorophenyl)-1-methyl-7-nitro-1H-1,4-benzodiazepin-2(3H)-one(flunitrazepam), 7-chloro-1-(2-diethylaminoethyl)-5-(2-fluorophenyl)-1H1,4-benzodiazepin-2(3H)-one (flurazepam), 7-chloro-5-phenyl-1-(2,2,2-trifluoroethyl)-1H-1,4-benzodiazepin-2(3H)-one (halazepam), 10-bromo-11b-(2-fluorophenyl)-2,3,7,11b-tetrahydro[1,3] oxazolyl[3,2-d] [1,4] benzodiazepin-6(5H)-one (haloxazolam), heroin, 4,5α-epoxy-3-methoxy-17-methyl-6-morphinanone (hydrocodone), 4,5α-epoxy-3-hydroxy-17-methyl-6-morphinanone (hydromorphone), hydroxypethidine, isomethadone, hydroxymethyl morphinane, 11-chloro-8,12b-dihydro-2,8-dimethyl-12b-phenyl-4H-[1,3] oxazino [3,2-d] [1,4] benzodiazepine-4,7(6H)-dione (ketazolam), 1-[4-(3-hydroxyphenyl)-1-methyl-4-piperidyl]-1-propanone (ketobemidone), (3S,6S)-6-dimethylamino-4,4-diphenyl-heptan-3-yl acetate (levacetylmethadol (LAAM)), (−)-6-dimethyl-amino-4,4-diphenol-3-heptanone (levomethadone), (−)-17-methyl-3-morphinanol (levorphanol), levophenacylmorphane, lofentanil, 6-(2-chlorophenyl)-2-(4-methyl-1-piperazinylmethylene)-8-nitro-2H-imidazo[1,2-a] [1,4]-benzodiazepin-1(4H)-one (loprazolam), 7-chloro-5-(2-chlorophenyl)-3-hydroxy-1H-1,4-benzodiazepin-2(3H)-one (lorazepam), 7-chloro-5-(2-chlorophenyl)-3-hydroxy-1-methyl-1H-1,4-benzodiazepin-2(3H)-one (lormetazepam), 5-(4-chlorophenyl)-2,5-dihydro-3H-imidazo[2,1-a] isoindol-5-ol (mazindol), 7-chloro-2,3-dihydro-1-methyl-5-phenyl-1H-1,4-benzodiazepine (medazepam), N-(3-chloropropyl)-α-methylphenethylamine (mefenorex), meperidine, 2-methyl-2-propyltrimethylene dicarbamate (meprobamate), meptazinol, metazocine, methylmorphine, N,α-dimethylphenethylamine (methamphetamine), (±)-6-dimethylamino-4,4-diphenyl-3-heptanone (methadone), 2-methyl-3-o-tolyl-4(3H)-quinazolinone (methaqualone), methyl [2-phenyl-2-(2-piperidyl)acetate] (methylphenidate), 5-ethyl-1-methyl-5-phenylbarbituric acid (methylphenobarbital), 3,3-diethyl-5-methyl-2,4-piperidinedione (methyprylon), metopon, 8-chloro-6-(2-fluorophenyl)-1-methyl-4H-imidazo[1,5-a] [1,4] benzodiazepine (midazolam), 2-(benzhydrylsulfinyl)-acetamide (modafinil), 4,5α-epoxy-17-methyl-7-morphinan-3,6α-diol (morphine), myrophine, (±)-trans-3-(1,1-dimethylheptyl)-7,8,10,10α-tetrahydro-1-hydroxy-6,6-dimethyl-6H-dibenzo [-b,d] pyran-9(6αH)-one (nabilone), nalbuphine, nalorphine, narceine, nicomorphine, 1-methyl-7-nitro-5-phenyl-1H-1,4-benzodiazepin-2(3H)-one (nimetazepam), 7-nitro-5-phenyl-1H-1,4-benzodiazepin-2(3H)-one (nitrazepam), 7-chloro-5-phenyl-1H-1,4-benzodiazepin-2(3H)-one (nordazepam), norlevorphanol, 6-dimethylamino-4,4-diphenyl-3-hexanone (normethadone), normorphine, norpipanone, the exudation for the plants belonging to the species *Papaver somniferum* (opium), 7-chloro-3-hydroxy-5-phenyl-1H-1,4-benzodiazepin-2 (3H)-one (oxazepam), (cis-trans)-10-chloro-2,3,7,11b-tetrahydro-2-methyl-11b-phenyloxazolo[3,2-d] [1,4] benzodiazepin-6-(5H)-one (oxazolam), 4,5α-epoxy-14-hydroxy-3-methoxy-17-methyl-6-morphinanone (oxycodone), oxymorphone, plants and parts of plants belonging to the species *Papaver somniferum* (including the subspecies *setigerum*), *papaveretum*, 2-imino-5-phenyl-4-oxazolidinone (pernoline), 1,2,3,4,5,6-hexahydro-6,11-dimethyl-3-(3-methyl-2-butenyl)-2,6-methano-3-benzazocin-8-ol (pentazocine), 5-ethyl-5-(1-methylbutyl)-barbituric acid (pentobarbital), ethyl (1-methyl-4-phenyl-4-piperidine carboxylate) (pethidine), phenadoxone, phenomorphan, phenazocine, phenoperidine, piminodine, pholcodine, 3-methyl-2-phenylmorpholine (phenmetrazine), 5-ethyl-5-phenylbarbituric acid (phenobarbital), α,α-dimethylphenethylamine (phentermine), 7-chloro-5-phenyl-1-(2-propynyl)-1H-1,4-benzodiazepin-2(3H)-one (pinazepam), α-(2-piperidyl)benzhydryl alcohol (pipradrol), 1'-(3-cyano-3,3-diphenylpropyl)[1,4'-bipiperidine]-4'-carboxamide (piritramide), 7-chloro-1-(cyclopropylmethyl)-5-phenyl-1H-1,4-benzodiazepin-2(3H)-one (prazepam), profadol, proheptazine, promedol, properidine, propoxyphene, N-(1-methyl-2-piperidinoethyl)-N-(2-pyridyl) propionamide, methyl {3-[4-methoxycarbonyl-4-(N-phenylpropanamido) piperidino] propanoate} (remifentanil), 5-sec-butyl-5-ethylbarbituric acid (secbutabarbital), 5-allyl-5-(1-methylbutyl)-barbituric acid (secobarbital), N-{4-methoxymethyl-1-[2-(2-thienyl)ethyl]-4-piperidyl}-propionanilide (sufentanil), 7-chloro-2-hydroxy-methyl-5-phenyl-1H-1, 4-benzodiazepin-2(3H)-one (temazepam), 7-chloro-5-(1-cyclohexenyl)-1-methyl-1H-1,4-benzodiazepin-2(3H)-one (tetrazepam), ethyl (2-dimethylamino-1-phenyl-3-cyclohexene-1-carboxylate) (tilidine (cis and trans)), tramadol, 8-chloro-6-(2-chlorophenyl)-1-methyl-4H-[1,2,4] triazolo [4,3-a] [1,4] benzodiazepine (triazolam), 5-(1-methylbutyl)-5-vinylbarbituric acid (vinylbital), (1R,2R)-3-(3-dimethylamino-1-ethyl-2-methyl-propyl)-phenol, (1R,2R,4S)-2-(dimethylamino)methyl-4-(p-fluorobenzyloxy)-1-(m-methoxyphenyl) cyclohexanol, (1R,2R)-3-(2-dimethylaminomethyl-cyclohexyl) phenol, (1S,2S)-3-(3-dimethylamino-1-ethyl-2-methyl-propyl) phenol, (2R,3R)-1-dimethylamino-3(3-methoxyphenyl)-2-methyl-pentan-3-ol, (1RS,3RS,6RS)-6-dimethylaminomethyl-1-(3-methoxyphenyl)-cyclohexan-1,3-diol, preferably as racemate, 3-(2-dimethylaminomethyl-1-hydroxy-cyclohexyl) phenyl 2-(4-isobutyl-phenyl)-propionate, 3-(2-dimethylaminomethyl-1-hydroxy-cyclohexyl)phenyl 2-(6-methoxy-naphthalen-2-yl)-propionate, 3-(2-dimethylaminomethyl-cyclohex-1-enyl)-phenyl 2-(4-isobutyl-phenyl)-propionate, 3-(2-dimethylaminomethyl-cyclohex-1-enyl)-phenyl 2-(6-methoxy-naphthalen-2-yl)-propionate, (RR-SS)-2-acetoxy-4-trifluoromethyl-benzoic acid 3-(2-dimethylaminomethyl-1-hydroxy-cyclohexyl)-phenyl ester, (RR-SS)-2-hydroxy-4-trifluoromethyl-benzoic acid 3-(2-dimethylaminomethyl-1-hydroxy-cyclohexyl)-phenyl ester, (RR-SS)-4-chloro-2-hydroxy-benzoic acid 3-(2-dimethylaminomethyl-1-hydroxy-cyclohexyl)-phenyl ester, (RR-SS)-2-hydroxy-4-methyl-benzoic acid 3-(2-dimethylaminomethyl-1-hydroxy-cyclohexyl)-phenyl ester, (RR-SS)-2-hydroxy-4-methoxy-benzoic acid 3-(2-dimethylaminomethyl-1-hydroxy-cyclohexyl)-phenyl ester, (RR-SS)-2-hydroxy-5-nitro-benzoic acid 3-(2-dimethylaminomethyl-1-hydroxy-cyclohexyl)-phenyl ester, (RR-SS)-2',4'-difluoro-3-hydroxy-biphenyl-4-carboxylic acid 3-(2-dimethylaminomethyl-1-hydroxy-cyclohexyl)-phenyl ester and corresponding stereoisomeric compounds, the corresponding derivatives thereof in each case, in particular amides, esters or ethers, and the physiologically acceptable compounds thereof in each case, in particular the salts and solvates thereof, particularly preferably hydrochlorides.

The dosage form according to the invention is in particular suitable for preventing abuse of an opioid active ingredient selected from the group comprising oxycodone, hydromorphone, morphine, tramadol and the physiologically acceptable derivatives or compounds thereof, preferably the salts and solvates thereof, preferably the hydrochlorides thereof.

The dosage form according to the invention is furthermore in particular suitable for preventing abuse of an opioid active ingredient selected from the group comprising (1R,2R)-3-(3-dimethylamino-1-ethyl-2-methyl-propyl)-phenol, (2R,3R)-1-dimethylamino-3-(3-methoxy-phenyl)-2-methyl-pentan-3-ol, (1RS,3RS,6RS)-6-dimethylaminomethyl-1-(3-methoxy-phenyl)-cyclohexane-1,3-diol, (1R,2R)-3-(2-dimethylaminoethyl-cyclohexyl)-phenol, the physiologically acceptable salts thereof, preferably hydrochlorides, physiologically acceptable enantiomers, stereoisomers, diastereomers and racemates and the physiologically acceptable derivatives thereof, preferably ethers, esters or amides.

These compounds and processes for the production thereof are described in EP-A-693475 or EP-A-780369. The corresponding descriptions are hereby introduced as a reference and are deemed to be part of the disclosure.

In order to achieve the necessary breaking strength of the dosage form according to the invention, at least one synthetic or natural polymer (C) is used which has a breaking strength, measured using the method disclosed in the present application, of at least 500 N. At least one polymer selected from the group comprising polyalkylene oxides, preferably polymethylene oxide, polyethylene oxide, polypropylene oxide; polyethylene, polypropylene, polyvinyl chloride, polycarbonate, polystyrene, polyacrylate, copolymers thereof, and mixtures of at least two of the stated polymers is preferably used for this purpose. High molecular weight thermoplastic polyalkylene oxides are preferred. High molecular weight polyethylene oxides with a molecular weight of at least 0.5 million, preferably of at least 1 million up to 15 million, determined by rheological measurements, are particularly preferred. These polymers have a viscosity at 25° C. of 4500 to 17600 cP, measured on a 5 wt. % aqueous solution using a model RVF Brookfield viscosimeter (spindle no. 2/rotational speed 2 rpm), of 400 to 4000 cP, measured on a 2 wt. % aqueous solution using the stated viscosimeter (spindle no. 1 or 3/rotational speed 10 rpm) or of 1650 to 10000 cP, measured on a 1 wt. % aqueous solution using the stated viscosimeter (spindle no. 2/rotational speed 2 rpm).

The polymers are preferably used in powder form. They may be soluble in water.

In order to achieve the necessary breaking strength of the dosage form according to the invention, it is furthermore possible additionally to use at least one natural or synthetic wax (D) with a breaking strength, measured using the method disclosed in the present application, of at least 500 N. Waxes with a softening point of at least 60° C. are preferred. Carnauba wax and beeswax are particularly preferred. Carnauba wax is very particularly preferred. Carnauba wax is a natural wax which is obtained from the leaves of the carnauba palm and has a softening point of at least 80° C. When the wax component is additionally used, it is used together with at least one polymer (C) in quantities such that the dosage form has a breaking strength of at least 500 N.

Component (C) is preferably used in an amount of 20 to 99.9 wt. %, particularly preferably of at least 30 wt. %, very particularly preferably of at least 40 wt. %, relative to the total weight of the dosage form.

Auxiliary substances (B) which may be used are those known auxiliary substances which are conventional for the formulation of solid dosage forms. These are preferably plasticisers, such as polyethylene glycol, auxiliary substances which influence active ingredient release, preferably hydrophobic or hydrophilic, preferably hydrophilic polymers, very particularly preferably hydroxypropylcellulose, and/or antioxidants. Suitable antioxidants are ascorbic acid, butylhydroxyanisole, butylhydroxytoluene, salts of ascorbic acid, monothioglycerol, phosphorous acid, vitamin C, vitamin E and the derivatives thereof, sodium bisulfite, particularly preferably butylhydroxytoluene (BHT) or butylhydroxyanisole (BHA) and α-tocopherol.

The antioxidant is preferably used in quantities of 0.01 to 10 wt. %, preferably of 0.03 to 5 wt. %, relative to the total weight of the dosage form.

The dosage forms according to the invention are distinguished in that, due their hardness, they cannot be pulverised in conventional comminution means available to an abuser, such as a mortar and pestle. This virtually rules out oral or parenteral, in particular intravenous or nasal abuse. However, in order to prevent any possible abuse of the dosage form according to the invention, the dosage forms according to the invention may, in a preferred embodiment, contain further agents which complicate or prevent abuse as auxiliary substances (B).

The abuse-proofed dosage form according to the invention, which comprises, apart from one or more active ingredients with abuse potential, at least one hardening polymer (C) and optionally at least one wax (D), may accordingly also comprise at least one of the following components (a)-(e) as auxiliary substances (B):
(a) at least one substance which irritates the nasal passages and/or pharynx, (b) at least one viscosity-increasing agent, which, with the assistance of a necessary minimum quantity of an aqueous liquid, forms a gel with the extract obtained from the dosage form, which gel preferably remains visually distinguishable when introduced into a further quantity of an aqueous liquid,
(c) at least one antagonist for each of the active ingredients with abuse potential,
(d) at least one emetic,
(e) at least one dye as an aversive agent,
(f) at least one bitter substance.

Components (a) to (f) are additionally each individually suitable for abuse-proofing the dosage form according to the invention. Accordingly, component (a) is preferably suitable for proofing the dosage form against nasal, oral and/or parenteral, preferably intravenous, abuse, component (b) is preferably suitable for proofing against parenteral, particularly preferably intravenous and/or nasal abuse, component (c) is preferably suitable for proofing against nasal and/or parenteral, particularly preferably intravenous, abuse, component (d) is preferably suitable for proofing against parenteral, particularly preferably intravenous, and/or oral and/or nasal abuse, component (e) is suitable as a visual deterrent against oral or parenteral abuse and component (f) is suitable for proofing against oral or nasal abuse. Combined use according to the invention of at least one of the above-stated components makes it possible still more effectively to prevent abuse of dosage forms according to the invention.

In one embodiment, the dosage form according to the invention may also comprise two or more of components (a)-(f) in a combination, preferably (a), (b) and optionally (c) and/or (f) and/or (e) or (a), (b) and optionally (d) and/or (f) and/or (e).

In another embodiment, the dosage form according to the invention may comprise all of components (a)-(f).

If the dosage form according to the invention comprises component (a) to counter abuse, substances which irritate the nasal passages and/or pharynx which may be considered according to the invention are any substances which, when administered via the nasal passages and/or pharynx, bring about a physical reaction which is either so unpleasant for the abuser that he/she does not wish to or cannot continue administration, for example burning, or physiologically counteracts taking of the corresponding active ingredient, for example due to increased nasal secretion or sneezing. These substances which conventionally irritate the nasal passages and/or pharynx may also bring about a very unpleasant sensation or even unbearable pain when administered parenterally, in particular intravenously, such that the abuser does not wish to or cannot continue taking the substance.

Particularly suitable substances which irritate the nasal passages and/or pharynx are those which cause burning, itching, an urge to sneeze, increased formation of secretions or a combination of at least two of these stimuli. Appropriate substances and the quantities thereof which are conventionally to be used are known per se to the person skilled or may be identified by simple preliminary testing.

The substance which irritates the nasal passages and/or pharynx of component (a) is preferably based on one or more constituents or one or more plant parts of at least one hot substance drug.

Corresponding hot substance drugs are known per se to the person skilled in the art and are described, for example, in "Pharmazeutische Biologie—Drogen und ihre Inhaltsstoffe" by Prof. Dr. Hildebert Wagner, 2nd., revised edition, Gustav Fischer verlag, Stuttgart-New York, 1982, pages 82 et seq. The corresponding description is hereby introduced as a reference and is deemed to be part of the disclosure.

A dosage unit is taken to mean a separate or separable administration unit, such as for example a tablet or a capsule.

One or more constituents of at least one hot substance drug selected from the group consisting of *Allii sativi bulbus* (garlic), *Asari rhizoma cum herba* (Asarum root and leaves), *Calami rhizoma* (calamus root), *Capsici fructus* (capsicum), *Capsici fructus acer* (cayenne pepper), *Curcumae longae rhizoma* (turmeric root), *Curcumae xanthorrhizae rhizoma* (Javanese turmeric root), *Galangae rhizoma* (galangal root), *Myristicae semen* (nutmeg), *Piperis nigri fructus* (pepper), *Sinapis albae semen* (white mustard seed), *Sinapis nigri semen* (black mustard seed), *Zedoariae rhizoma* (zedoary root) and *Zingiberis rhizoma* (ginger root), particularly preferably from the group consisting of *Capsici fructus* (capsicum), *Capsici fructus acer* (cayenne pepper) and *Piperis nigri fructus* (pepper) may preferably be added as component (a) to the dosage form according to the invention.

The constituents of the hot substance drugs preferably comprise o-methoxy(methyl)phenol compounds, acid amide compounds, mustard oils or sulfide compounds or compounds derived therefrom.

Particularly preferably, at least one constituent of the hot substance drugs is selected from the group consisting of myristicin, elemicin, isoeugenol, a-asarone, safrole, gingerols, xanthorrhizol, capsaicinoids, preferably capsaicin, capsaicin derivatives, such as N-vanillyl-9E-octadecenamide, dihydrocapsaicin, nordihydrocapsaicin, homocapsaicin, norcapsaicin and nomorcapsaicin, piperine, preferably trans-piperine, glucosinolates, preferably based on non-volatile mustard oils, particularly preferably based on p-hydroxybenzyl mustard oil, methylmercapto mustard oil or methylsulfonyl mustard oil, and compounds derived from these constituents.

The dosage form according to the invention may preferably contain the plant parts of the corresponding hot substance drugs in a quantity of 0.01 to 30 wt. %, particularly preferably of 0.1 to 0.5 wt. %, in each case relative to the total weight of the dosage unit.

If one or more constituents of corresponding hot substance drugs are used, the quantity thereof in a dosage unit according to the invention preferably amounts to 0.001 to 0.005 wt. %, relative to the total weight of the dosage unit.

Another option for preventing abuse of the dosage form according to the invention consists in adding at least one viscosity-increasing agent as a further abuse-preventing component (b) to the dosage form, which, with the assistance of a necessary minimum quantity of an aqueous liquid, forms a gel with the extract obtained from the dosage form, which gel is virtually impossible to administer safely and preferably remains visually distinguishable when introduced into a further quantity of an aqueous liquid.

For the purposes of the present invention, visually distinguishable means that the active ingredient-containing gel formed with the assistance of a necessary minimum quantity of aqueous liquid, when introduced, preferably with the assistance of a hypodermic needle, into a further quantity of aqueous liquid at 37° C., remains substantially insoluble and cohesive and cannot straightforwardly be dispersed in such a manner that it can safely be administered parenterally, in particular intravenously. The material preferably remains visually distinguishable for at least one minute, preferably for at least 10 minutes.

The increased viscosity of the extract makes it more difficult or even impossible for it to be passed through a needle or injected. If the gel remains visually distinguishable, this means that the gel obtained on introduction into a further quantity of aqueous liquid, for example by injection into blood, initially remains in the form of a largely cohesive thread, which, while it may indeed be broken up into smaller fragments, cannot be dispersed or even dissolved in such a manner that it can safely be administered parenterally, in particular intravenously. In combination with at least one optionally present component (a) to (e), this additionally leads to unpleasant burning, vomiting, bad flavour and/or visual deterrence.

Intravenous administration of such a gel would most probably result in obstruction of blood vessels, associated with serious harm to the health of the abuser.

In order to verify whether a viscosity-increasing agent is suitable as component (b) for use in the dosage form according to the invention, the active ingredient is mixed with the viscosity-increasing agent and suspended in 10 ml of water at a temperature of 25° C. If this results in the formation of a gel which fulfils the above-stated conditions, the corresponding viscosity-increasing agent is suitable for preventing or averting abuse of the dosage forms according to the invention.

If component (b) is added to the dosage form according to the invention, one or more viscosity-increasing agents are used which are selected from the group comprising microcrystalline cellulose with 11 wt. % carboxymethylcellulose sodium (Avicel® RC 591), carboxymethylcellulose sodium (Blanose®, CMC-Na C300P®, Frimulsion BLC-5®, Tylose C300 P®), polyacrylic acid (Carbopol® 980 NF, Carbopol® 981), locust bean flour (Cesagum® LA-200, Cesagum® LID/150, Cesagum® LN-1), pectins, preferably from citrus fruits or apples (Cesapectin® HM Medium Rapid Set), waxy maize starch (C*Gel 04201®), sodium alginate (Frimulsion ALG (E401)®), guar flour (Frimulsion BM®, Polygum 26/1-75®), iota carrageen (Frimulsion D021®), karaya gum, gellan gum (Kelcogel F®, Kelcogel LT100®), galactomannan (Meyprogat 150 ®), tara bean flour (Polygum 43/1®), propylene glycol alginate (Protanal-Ester SD-LBO), sodium hyaluronate, tragacanth, tara gum (Vidogum SP 200®), fermented polysaccharide welan gum (K1A96), xanthan gum (Xantural 180®). Xanthans are particularly preferred. The names stated in brackets are the trade names by which the materials are known commercially. In general, a quantity of 0.1 to 20 wt. %, particularly preferably of 0.1 to 15 wt. % of the stated viscosity-increasing agent(s) is sufficient to fulfil the above-stated conditions.

The component (b) viscosity-increasing agents, where provided, are preferably present in the dosage form according to the invention in quantities of ≧5 mg per dosage unit, i.e. per administration unit.

In a particularly preferred embodiment of the present invention, the viscosity-increasing agents used as component (b) are those which, on extraction from the dosage form with the necessary minimum quantity of aqueous liquid, form a gel which encloses air bubbles. The resultant gels are distinguished by a turbid appearance, which provides the potential abuser with an additional optical warning and discourages him/her from administering the gel parenterally.

Component (C) may also optionally serves as an additional viscosity-increasing agent which, with the assistance of a minimum necessary quantity of an aqueous liquid, forms a gel.

It is also possible to formulate the viscosity-increasing agent and the other constituents in the dosage form according to the invention in a mutually spatially separated arrangement.

In order to discourage and prevent abuse, the dosage form according to the invention may furthermore comprise component (c), namely one or more antagonists for the active ingredient or active ingredients with abuse potential, wherein the antagonists are preferably spatially separated from the remaining constituents of the invention dosage according to the form and, when correctly used, do not exert any effect.

Suitable antagonists for preventing abuse of the active ingredients are known per se to the person skilled in the art and may be present in the dosage form according to the invention as such or in the form of corresponding derivatives, in particular esters or ethers, or in each case in the form of corresponding physiologically acceptable compounds, in particular in the form of the salts or solvates thereof.

If the active ingredient present in the dosage form is an opioid, the antagonist used is preferably an antagonist selected from the group comprising naloxone, naltrexone, nalmefene, nalid, nalmexone, nalorphine or naluphine, in each case optionally in the form of a corresponding physiologically acceptable compound, in particular in the form of a base, a salt or solvate. The corresponding antagonists, where component (c) is provided, are preferably used in a quantity of ≧1 mg, particularly preferably in a quantity of 3 to 100 mg, very particularly preferably in a quantity of 5 to 50 mg per dosage form, i.e. per administration unit.

If the dosage form according to the invention comprises a stimulant as active ingredient, the antagonist is preferably a neuroleptic, preferably at least one compound selected from the group consisting of haloperidol, promethazine, fluphenazine, perphenazine, levomepromazine, thioridazine, perazine, chlorpromazine, chlorprothixine, zuclopentixol, flupentixol, prothipendyl, zotepine, benperidol, pipamperone, melperone and bromperidol.

The dosage form according to the invention preferably comprises these antagonists in a conventional therapeutic dose known to the person skilled in the art, particularly preferably in a quantity of twice to four times the conventional dose per administration unit.

If the combination to discourage and prevent abuse of the dosage form according to the invention comprises component (d), it may comprise at least one emetic, which is preferably present in a spatially separated arrangement from the other components of the dosage form according to the invention and, when correctly used, is intended not to exert its effect in the body.

Suitable emetics for preventing abuse of an active ingredient are known per se to the person skilled in the art and may be present in the dosage form according to the invention as such or in the form of corresponding derivatives, in particular esters or ethers, or in each case in the form of corresponding physiologically acceptable compounds, in particular in the form of the salts or solvates thereof.

An emetic based on one or more constituents of ipecacuanha (ipecac) root, preferably based on the constituent emetine may preferably be considered in the dosage form according to the invention, as are, for example, described in "Pharmazeutische Biologie—Drogen und ihre Inhaltsstoffe" by Prof. Dr. Hildebert Wagner, 2nd, revised edition, Gustav Fischer Verlag, Stuttgart, New York, 1982. The corresponding literature description is hereby introduced as a reference and is deemed to be part of the disclosure.

The dosage form according to the invention may preferably comprise the emetic emetine as component (d), preferably in a quantity of ≧3 mg, particularly preferably of ≧10 mg and very particularly preferably in a quantity of ≧20 mg per dosage form, i.e. administration unit.

Apomorphine may likewise preferably be used as an emetic in the abuse-proofing according to the invention, preferably in a quantity of preferably ≧3 mg, particularly preferably of ≧5 mg and very particularly preferably of ≧7 mg per administration unit.

If the dosage form according to the invention contains component (e) as a further abuse-preventing auxiliary substance, the use of a such a dye brings about an intense coloration of a corresponding aqueous solution, in particular when the attempt is made to extract the active ingredient for parenteral, preferably intravenous administration, which coloration may act as a deterrent to the potential abuser. Oral abuse, which conventionally begins by means of aqueous extraction of the active ingredient, may also be prevented by this coloration. Suitable dyes and the quantities required for the necessary deterrence may be found in WO 03/015531, wherein the corresponding disclosure should be deemed to be part of the present disclosure and is hereby introduced as a reference.

If the dosage form according to the invention contains component (f) as a further abuse-preventing auxiliary substance, this addition of at least one bitter substance and the consequent impairment of the flavour of the dosage form additionally prevents oral and/or nasal abuse.

Suitable bitter substances and the quantities effective for use may be found in U.S.-2003/0064099 A1, the corresponding disclosure of which should be deemed to be the disclosure of the present application and is hereby introduced as a reference. Suitable bitter substances are preferably aromatic oils, preferably peppermint oil, eucalyptus oil, bitter almond oil, menthol, fruit aroma substances, preferably aroma substances from lemons, oranges, limes, grapefruit or mixtures thereof, and/or denatonium benzoate (Bitrex®). Denatonium benzoate is particularly preferred.

The solid dosage form according to the invention is suitable to be taken orally, vaginally or rectally, preferably orally. The dosage form is preferably not in film form. The dosage form according to the invention may assume multiparticulate form, preferably in the form of microtablets, microcapsules, micropellets, granules, spheroids, beads or pellets, optionally packaged in capsules or pressed into tablets, preferably for oral administration. The multiparticulate forms preferably have a size or size distribution in the range from 0.1 to 3 mm, particularly preferably in the range from 0.5 to 2 mm. Depending on the desired dosage form, conventional auxiliary substances (B) are optionally also used for the formulation of the dosage form.

The solid, abuse-proofed dosage form according to the invention is preferably produced by thermoforming with the assistance of an extruder without any observable consequent discoloration of the extrudates.

In order to investigate the extent of discoloration due to this thermoforming, the colour of the mixture of starting components of which the dosage form consists is first determined without addition of a colour-imparting component, such as for example a colouring pigment or an intrinsically coloured component (for example α-tocopherol). This composition is then thermoformed according to the invention, wherein all process steps, including cooling of the extrudate, are performed under an inert gas atmosphere. By way of comparison, the same composition is produced by the same process, but without an inert gas atmosphere. The colour of the dosage form produced according to the invention from the starting composition and of the dosage form produced by way of comparison is determined. The determination is performed with the assistance of "Munsell Book of Color" from Munsell Color Company Baltimore, Md., USA, 1966 edition. If the colour of the dosage form thermoformed according to the invention has a colour with identification no. N 9.5, but at most a colour with the identification no. 5Y 9/1, thermoforming is classed as being "without discoloration". If the dosage form has a colour with the identification no. 5Y 9/2 or greater, as determined according to the Munsell Book of Color, the thermoforming is classed as being "with discoloration".

Surprisingly, the dosage forms according to the invention exhibit no discoloration classed in accordance with the above classification, if the entire production process is performed under an inert gas atmosphere, preferably under a nitrogen atmosphere with the assistance of an extruder for thermoforming.

A present invention accordingly also provides a process for the production of the abuse-proofed dosage forms according to the invention, which process is characterised in that z) components (A), (B), (C) and the optionally present component (D) are mixed and the optionally present components a) to f) are co-mixed or, if necessary, are mixed separately with the addition of component (C) and optionally (D), y) the resultant mixture or the resultant mixtures is/are heated in the extruder at least up to the softening point of component (C) and extruded through the outlet orifice of the extruder by application of force, x) the still plastic extrudate is singulated and formed into the dosage form or w) the cooled and optionally reheated singulated extrudate is formed into the dosage form, wherein process steps y) and x) and optionally process steps z) and w) are performed under an inert gas atmosphere, preferably a nitrogen atmosphere.

Mixing of the components according to process step z) may also proceed in the extruder.

Mixing of components (A), (B), (C) and optionally (D) and of the optionally present further components (a)-(f) and optionally components (C) and the optionally present component (D) may also optionally proceed in a mixer known to the person skilled in the art. The mixer may, for example, be a roll mixer, shaking mixer, shear mixer or compulsory mixer.

Before blending with the remaining components, component (C) and the optionally present component (D) is preferably provided according to the invention with an antioxidant. This may proceed by mixing the two components, (C) and the antioxidant, preferably by dissolving or suspending the antioxidant in a highly volatile solvent and homogeneously mixing this solution or suspension with component (C) and the optionally present component (D) and removing the solvent by drying, preferably under an inert gas atmosphere.

The dosage forms according to the invention which contain subunits with further auxiliary substances which prevent or complicate abuse may be produced by coextruding or separately extruding the mixtures according to z).

In any event, the, preferably molten, mixture or mixtures which has/have been heated in the extruder at least up to the softening point of component (C) is/are extruded from the extruder through a die with at least one bore.

The process according to the invention is preferably performed using conventional extruders, particularly preferably screw extruders, which may be equipped with one or two screws.

The extruder preferably comprises at least two temperature zones, with heating of the mixture at least up to the softening point of component (C) proceeding in the first zone, which is downstream from a feed zone and optionally mixing zone. The throughput of the mixture is preferably from 2.0 kg to 8.0 kg/hour.

After heating at least up to the softening point of component (C), the molten mixture is conveyed with the assistance of the screws, further homogenised, compressed or compacted such that, immediately before emerging from the extruder die, it exhibits a minimum pressure of 5 bar, preferably of at least 10 bar, and is extruded through the die as an extruded strand or strands, depending on the number of bores which the die comprises. The die geometry or the geometry of the bores is freely selectable. The die or the bores may accordingly exhibit a round, oblong or oval cross-section, wherein the round cross-section preferably has a diameter of 0.1 mm to 15 mm and the oblong cross-section preferably has a maximum lengthwise extension of 21 mm and a crosswise extension of 10 mm. Preferably, the die or the bores have a round cross-section. The casing of the extruder used according to the invention may be heated or cooled. The corresponding temperature control, i.e. heating or cooling, is so arranged that the mixture to be extruded exhibits at least an average temperature (product temperature) corresponding to the softening temperature of component (C) and does not rise above a temperature at which the active substance with abuse potential which is to be processed may be damaged. Preferably, the temperature of the mixture to be extruded is adjusted to below 180° C., preferably below 150° C., but at least to the softening temperature of component (C).

After extrusion of the molten mixture and optional cooling of the extruded strand or extruded strands, the extrudates are preferably comminuted. This comminution may preferably be performed by cutting up the extrudates by means of revolving or rotating knives, water jet cutters, wires, blades or with the assistance of laser cutters.

An inert gas atmosphere is not necessary for intermediate or final storage of the optionally singulated extrudate or the final shape of the dosage form according to the invention.

The singulated extrudate may be pelletised with conventional methods or be press-moulded into tablets in order to impart the final shape to the dosage form. It is, however, also possible not to singulate the extruded strands and, with the assistance of contrarotating calender rolls comprising opposing recesses in their outer sleeve, to form them into the final shape, preferably a tablet, and to singulate these by conventional methods.

Should the optionally singulated extrudate not immediately be formed into the final shape, but instead cooled for storage, after the period of storage an inert gas atmosphere, preferably a nitrogen atmosphere, should be provided and must be maintained during heating of the stored extrudate up until plasticisation and definitive shaping to yield the dosage form.

The application of force in the extruder onto the at least plasticised mixture is adjusted by controlling the rotational speed of the conveying device in the extruder and the geometry thereof and by dimensioning the outlet orifice in such a manner that the pressure necessary for extruding the plasticised mixture is built up in the extruder, preferably immediately prior to extrusion. The extrusion parameters which, for each particular composition, are necessary to give rise to a dosage form with a breaking strength of at least 500 N, may be established by simple preliminary testing.

In a further preferred embodiment, the dosage form according to the invention assumes the form of a tablet, a capsule or is in the form of an oral osmotic therapeutic system (OROS), preferably if at least one further abuse-preventing component (a)-(f) is also present.

If components (c) and/or (d) and/or (f) are present in the dosage form according to the invention, care must be taken to ensure that they are formulated in such a manner or are present in such a low dose that, when correctly administered, the dosage form is able to bring about virtually no effect which impairs the patient or the efficacy of the active ingredient.

If the dosage form according to the invention contains component (d) and/or (f), the dosage must be selected such that, when correctly orally administered, no negative effect is caused. If, however, the intended dosage of the dosage form is exceeded in the event of abuse, nausea or an inclination to vomit or a bad flavour are produced. The particular quantity of component (d) and/or (f) which can still be tolerated by the patient in the event of correct oral administration may be determined by the person skilled in the art by simple preliminary testing.

If, however, irrespective of the fact that the dosage form according to the invention is virtually impossible to pulverise, the dosage form containing the components (c) and/or (d) and/or (f) is provided with protection, these components should preferably be used at a dosage which is sufficiently high that, when abusively administered, they bring about an intense negative effect on the abuser. This is preferably achieved by spatial separation of at least the active ingredient or active ingredients from components (c) and/or (d) and/or (f), wherein the active ingredient or active ingredients is/are present in at least one subunit (X) and components (c) and/or (d) and/or (f) is/are present in at least one subunit (Y), and wherein, when the dosage form is correctly administered, components (c), (d) and (f) do not exert their effect on taking and/or in the body and the remaining components of the formulation, in particular component (C) and optionally (D), are identical.

If the dosage form according to the invention comprises at least 2 of components (c) and (d) or (f), these may each be present in the same or different subunits (Y). Preferably, when present, all the components (c) and (d) and (f) are present in one and the same subunit (Y).

For the purposes of the present invention, subunits are solid formulations, which in each case, apart from conventional auxiliary substances known to the person skilled in the art, contain the active ingredient(s), at least one polymer (C) and the optionally present component (D) and optionally at least one of the optionally present components (a) and/or (b) and/or (e) or in each case at least one polymer (C) and optionally (D) and the antagonist(s) and/or emetic(s) and/or component (e) and/or component (f) and optionally at least one of the optionally present components (a) and/or (b). Care must here be taken to ensure that each of the subunits is formulated in accordance with the above-stated process.

One substantial advantage of the separated formulation of active ingredients from components (c) or (d) or (f) in subunits (X) and (Y) of the dosage form according to the invention is that, when correctly administered, components (c) and/or (d) and/or (f) are hardly released on taking and/or in the body or are released in such small quantities that they exert no effect which impairs the patient or therapeutic success or, on passing through the patient's body, they are only liberated in locations where they cannot be sufficiently absorbed to be effective. When the dosage form is correctly administered, preferably hardly any of components (c) and/or (d) and/or (f) is released into the patient's body or they go unnoticed by the patient.

The person skilled in the art will understand that the above-stated conditions may vary as a function of the particular components (c), (d) and/or (f) used and of the formulation of the subunits or the dosage form. The optimum formulation for the particular dosage form may be determined by simple preliminary testing. What is vital is that each subunit contains the polymer (C) and optionally component (D) and has been formulated in the above-stated manner.

Should, contrary to expectations, the abuser succeed in comminuting such a dosage form according to the invention, which comprises components (c) and/or (e) and/or (d) and/or (f) in subunits (Y), for the purpose of abusing the active ingredient and obtain a powder which is extracted with a suitable extracting agent, not only the active ingredient but also the particular component (c) and/or (e) and/or (f) and/or (d) will be obtained in a form in which it cannot readily be separated from the active ingredient, such that when the dosage form which has been tampered with is administered, in particular by oral and/or parenteral administration, it will exert its effect on taking and/or in the body combined with an additional negative effect on the abuser corresponding to component (c) and/or (d) and/or (f) or, when the attempt is made to extract the active ingredient, the coloration will act as a deterrent and so prevent abuse of the dosage form.

A dosage form according to the invention, in which the active ingredient or active ingredients is/are spatially separated from components (c), (d) and/or (e), preferably by formulation in different subunits, may be formulated in many different ways, wherein the corresponding subunits may each be present in the dosage form according to the invention, in any desired spatial arrangement relative to one another, provided that the above-stated conditions for the release of components (c) and/or (d) are fulfilled.

The person skilled in the art will understand that component(s) (a) and/or (b) which are optionally also present may preferably be formulated in the dosage form according to the invention both in the particular subunits (X) and (Y) and in the form of independent subunits corresponding to subunits (X) and (Y), provided that neither the abuse-proofing nor the active ingredient release in the event of correct administration is impaired by the nature of the formulation and the polymer (C) and optionally (D) is included in the formulation and formulation is carried out in accordance with the above-stated process in order to achieve the necessary hardness.

In a preferred embodiment of the dosage form according to the invention, subunits (X) and (Y) are present in multiparticulate form, wherein microtablets, microcapsules, micropellets, granules, spheroids, beads or pellets are preferred and the same form, i.e. shape, is selected for both subunit (X) and subunit (Y), such that it is not possible to separate subunits (X) from (Y) by mechanical selection. The multiparticulate forms are preferably of a size in the range from 0.1 to 3 mm, preferably of 0.5 to 2 mm.

The subunits (X) and (Y) in multiparticulate form may also preferably be packaged in a capsule or be pressed into a tablet, wherein the final formulation in each case proceeds in such a manner that the subunits (X) and (Y) are also retained in the resultant dosage form.

The multiparticulate subunits (X) and (Y) of identical shape should also not be visually distinguishable from one another so that the abuser cannot separate them from one another by simple sorting. This may, for example, be achieved by the application of identical coatings which, apart from this disguising function, may also incorporate further functions, such as, for example, controlled release of one or more active ingredients or provision of a finish resistant to gastric juices on the particular subunits.

The multiparticulate subunits may also be formulated as an oral dosage form as a slurry or suspension in pharmaceutically safe suspending media.

In a further preferred embodiment of the present invention, subunits (X) and (Y) are in each case arranged in layers relative to one another.

The layered subunits (X) and (Y) are preferably arranged for this purpose vertically or horizontally relative to one another in the dosage form according to the invention, wherein in each case one or more layered subunits (X) and one or more layered subunits (Y) may be present in the dosage form, such that, apart from the preferred layer sequences (X)-(Y) or (X)-(Y)-(X), any desired other layer sequences may be considered, optionally in combination with layers containing components (a) and/or (b).

Another preferred dosage form according to the invention is one in which subunit (Y) forms a core which is completely enclosed by subunit (X), wherein a separation layer (Z) may be present between said layers. Such a structure is preferably also suitable for the above-stated multiparticulate forms, wherein both subunits (X) and (Y) and an optionally present separation layer (Z), which must satisfy the hardness requirement according to the invention, are formulated in one and the same multiparticulate form. In a further preferred embodiment of the dosage form according to the invention, the subunit (X) forms a core, which is enclosed by subunit (Y), wherein the latter comprises at least one channel which leads from the core to the surface of the dosage form.

The dosage form according to the invention may comprise, between one layer of the subunit (X) and one layer of the subunit (Y), in each case one or more, preferably one, optionally swellable separation layer (Z) which serves to separate subunit (X) spatially from (Y).

If the dosage form according to the invention comprises the layered subunits (X) and (Y) and an optionally present separation layer (Z) in an at least partially vertical or horizontal arrangement, the dosage form preferably takes the form of a tablet, a coextrudate or a laminate.

In one particularly preferred embodiment, the entirety of the free surface of subunit (Y) and optionally at least part of the free surface of subunit(s) (X) and optionally at least part of the free surface of the optionally present separation layer(s) (Z) may be coated with at least one barrier layer (Z') which prevents release of component (c) and/or (e) and/or (d) and/or (f). The barrier layer (Z') must also fulfil the hardness conditions according to the invention.

Another particularly preferred embodiment of the dosage form according to the invention comprises a vertical or horizontal arrangement of the layers of subunits (X) and (Y) and at least one push layer (p) arranged therebetween, and optionally a separation layer (Z), in which dosage form the entirety of the free surface of layer structure consisting of subunits (X) and (Y), the push layer and the optionally present separation layer (Z) is provided with a semipermeable coating (E), which is permeable to a release medium, i.e. conventionally a physiological liquid, but substantially impermeable to the active ingredient and to component (c) and/or (d) and/or (f), and wherein this coating (E) comprises at least one opening for release of the active ingredient in the area of subunit (X).

A corresponding dosage form is known to the person skilled in the art, for example under the name oral osmotic therapeutic system (OROS), as are suitable materials and methods for the production thereof, inter alia from U.S. Pat. Nos. 4,612,008, 4,765,989 and U.S. Pat. No. 4,783,337. The corresponding descriptions are hereby introduced as a reference and are deemed to be part of the disclosure.

In a further preferred embodiment, the subunit (X) of the dosage form according to the invention is in the form of a tablet, the edge face of which and optionally one of the two main faces is covered with a barrier layer (Z') containing component (c) and/or (d) and/or (f).

The person skilled in the art will understand that the auxiliary substances of the subunit(s) (X) or (Y) and of the optionally present separation layer(s) (Z) and/or of the barrier layer(s) (Z') used in formulating the dosage form according to the invention will vary as a function of the arrangement thereof in the dosage form according to the invention, the mode of administration and as a function of the particular active ingredient of the optionally present components (a) and/or (b) and/or (e) and of component (c) and/or (d) and/or (f). The materials which have the requisite properties are in each case known per se to the person skilled in the art.

If release of component (c) and/or (d) and/or (f) from subunit (Y) of the dosage form according to the invention is prevented with the assistance of a cover, preferably a barrier layer, the subunit may consist of conventional materials known to the person skilled in the art, providing that it contains at least one polymer (C) and optionally (D) to fulfil the hardness condition of the dosage form according to the invention.

If a corresponding barrier layer (Z') is not provided to prevent release of component (c) and/or (d) and/or (f), the materials of the subunits should be selected such that release of the particular component (c) and/or (d) from subunit (Y) is virtually ruled out. The materials which are stated below to be suitable for production of the barrier layer may preferably be used for this purpose.

Preferred materials are those which are selected from the group comprising alkylcelluloses, hydroxyalkylcelluloses, glucans, scleroglucans, mannans, xanthans, copolymers of poly[bis(p-carboxyphenoxy)propane and sebacic acid, preferably in a molar ratio of 20:80 (commercially available under the name Polifeprosan 20®), carboxymethylcelluloses, cellulose ethers, cellulose esters, nitrocelluloses, polymers based on (meth)acrylic acid and the esters thereof, polyamides, polycarbonates, polyalkylenes, polyalkylene glycols, polyalkylene oxides, polyalkylene terephthalates, polyvinyl alcohols, polyvinyl ethers, polyvinyl esters, halogenated polyvinyls, polyglycolides, polysiloxanes and polyurethanes and the copolymers thereof.

Particularly suitable materials may be selected from the group comprising methylcellulose, ethylcellulose, hydroxypropylcellulose, hydroxypropylmethylcellulose, hydroxybutylmethylcellulose, cellulose acetate, cellulose propionate (of low, medium or high molecular weight), cellulose acetate propionate, cellulose acetate butyrate, cellulose acetate phthalate, carboxymethylcellulose, cellulose triacetate, sodium cellulose sulfate, polymethyl methacrylate, polyethyl methacrylate, polybutyl methacrylate, polyisobutyl methacrylate, polyhexyl methacrylate, polyisodecyl methacrylate, polylauryl methacrylate, polyphenyl methacrylate, polymethyl acrylate, polyisopropyl acrylate, polyisobutyl acrylate, polyoctadecyl acrylate, polyethylene, low density polyethylene, high density polyethylene, polypropylene, polyethylene glycol, polyethylene oxide, polyethylene terephthalate, polyvinyl alcohol, polyvinyl isobutyl ether, polyvinyl acetate and polyvinyl chloride.

Particularly suitable copolymers may be selected from the group comprising copolymers of butyl methacrylate and isobutyl methacrylate, copolymers of methyl vinyl ether and maleic acid with high molecular weight, copolymers of methyl vinyl ether and maleic acid monoethyl ester, copolymers of methyl vinyl ether and maleic anhydride and copolymers of vinyl alcohol and vinyl acetate. Further materials which are particularly suitable for formulating the barrier layer are starch-filled polycaprolactone (WO98/20073), aliphatic polyesteramides (DE 19 753 534 A1, DE 19 800 698 A1, EP 0 820 698 A1), aliphatic and aromatic polyester urethanes (DE 19822979), polyhydroxyalkanoates, in particular polyhydroxybutyrates, polyhydroxyvalerates, casein (DE 4 309 528), polylactides and copolylactides (EP 0 980 894 A1). The corresponding descriptions are hereby introduced as a reference and are deemed to be part of the disclosure.

The above-stated materials may optionally be blended with further conventional auxiliary substances known to the person skilled in the art, preferably selected from the group comprising glyceryl monostearate, semi-synthetic. triglyceride derivatives, semi-synthetic glycerides, hydrogenated castor oil, glyceryl palmitostearate, glyceryl behenate, polyvinylpyrrolidone, gelatine, magnesium stearate, stearic acid, sodium stearate, talcum, sodium benzoate, boric acid and colloidal silica, fatty acids, substituted triglycerides, glycerides, polyoxyalkylene glycols and the derivatives thereof.

If the dosage form according to the invention comprises a separation layer (Z'), said layer, like the uncovered subunit (Y), may preferably consist of the above-stated materials described for the barrier layer. The person skilled in the art will understand that release of the active ingredient or of component (c) and/or (d) from the particular subunit may be controlled by the thickness of the separation layer.

The dosage form according to the invention exhibits controlled release of the active ingredient. It is preferably suitable for twice daily administration to patients.

The dosage form according to the invention may comprise one or more active ingredients at least partially in controlled release form, wherein controlled release may be achieved with the assistance of conventional materials and methods known to the person skilled in the art, for example by embedding the active ingredient in a controlled release matrix or by the application of one or more controlled release coatings. Active ingredient release must, however, be controlled such that the above-stated conditions are fulfilled in each case, for example that, in the event of correct administration of the dosage form, the active ingredient or active ingredients are virtually completely released before the optionally present component (c) and/or (d) can exert an impairing effect. Addition of materials effecting controlled release must moreover not impair the necessary hardness.

Controlled release from the dosage form according to the invention is preferably achieved by embedding the active ingredient in a matrix. The auxiliary substances acting as matrix materials control active ingredient release. Matrix materials may, for example, be hydrophilic, gel-forming materials, from which active ingredient release proceeds mainly by diffusion, or hydrophobic materials, from which active ingredient release proceeds mainly by diffusion from the pores in the matrix.

Physiologically acceptable, hydrophobic materials which are known to the person skilled in the art may be used as matrix materials. Polymers, particularly preferably cellulose ethers, cellulose esters and/or acrylic resins are preferably used as hydrophilic matrix materials. Ethylcellulose, hydroxypropylmethylcellulose, hydroxypropylcellulose, hydroxymethylcellulose, poly(meth)acrylic acid and/or the derivatives thereof, such as the salts, amides or esters thereof are very particularly preferably used as matrix materials.

Matrix materials prepared from hydrophobic materials, such as hydrophobic polymers, waxes, fats, long-chain fatty acids, fatty alcohols or corresponding esters or ethers or mixtures thereof are also preferred. Mono- or diglycerides of C12-C30 fatty acids and/or C12-C30 fatty alcohols and/or waxes or mixtures thereof are particularly preferably used as hydrophobic materials.

It is also possible to use mixtures of the above-stated hydrophilic and hydrophobic materials as matrix materials.

Component (C) and the optionally present component (D), which serve to achieve the breaking strength of at least 500 N which is necessary according to the invention may furthermore also optionally serve as additional matrix materials.

If the dosage form according to the invention is intended for oral administration, it may also preferably comprise a coating which is resistant to gastric juices and dissolves as a function of the pH value of the release environment. By means of this coating, it is possible to ensure that the dosage form according to the invention passes through the stomach undissolved and the active ingredient is only released in the intestines. The coating which is resistant to gastric juices preferably dissolves at a pH value of between 5 and 7.5.

Corresponding materials and methods for the controlled release of active ingredients and for the application of coatings which are resistant to gastric juices are known to the person skilled in the art, for example from "Coated Pharmaceutical Dosage Forms—Fundamentals, Manufacturing Techniques, Biopharmaceutical Aspects, Test Methods and Raw Materials" by Kurt H. Bauer, K. Lehmann, Hermann P. Osterwald, Rothgang, Gerhart, 1st edition, 1998, Medpharm Scientific Publishers. The corresponding literature description is hereby introduced as a reference and is deemed to be part of the disclosure.

Method for Determining Breaking Strength

In order to verify whether a polymer may be used as component (C) or (D), the polymer is pressed to form a tablet with a diameter of 10 mm and a height of 5 mm using a force of 150 N at a temperature which at least corresponds to the softening point of the polymer and is determined with the assistance of a DSC diagram of the polymer. Using tablets produced in this manner, breaking strength is determined with the apparatus described below in accordance with the method for determining the breaking strength of tablets published in the European Pharmacopoeia 1997, page 143-144, method no. 2.9.8. The apparatus used for the measurement is a "Zwick z 2.5" materials tester, Fmax=2.5 kN with a maximum draw of 1150 mm, which should be set up with 1 column and 1 spindle, a clearance behind of 100 mm and a test speed adjustable between 0.1 and 800 mm/min together with testcontrol software. Measurement is performed using a pressure piston with screw-in inserts and a cylinder (diam. 10 mm), a force transducer, Fmax. 1 kN, diameter=8 mm, class 0.5 from 10 N, class 1 from 2 N to ISO 7500-1, with manufacturer's test certificate M to DIN 55350-18 (Zwick gross force Fmax=1.45 kN) (all apparatus from Zwick GmbH & Co. KG, Ulm, Germany) with order no. BTC-FR 2.5 TH. D09 for the tester, order no. BTC-LC 0050N. P01 for the force transducer, order no. BO 70000 S06 for the centring device.

FIG. 1 shows the measurement of the breaking strength of a tablet, in particular the tablet (4) adjustment device (6) used for this purpose before and during the measurement. To this end, the tablet (4) is held between the upper pressure plate (1) and the lower pressure plate (3) of the force application apparatus (not shown) with the assistance of two 2-part clamping devices, which are in each case firmly fastened (not shown) with the upper and lower pressure plate once the spacing (5) necessary for accommodating and centring the tablet to be measured has been established. The spacing (5) may be established by moving the 2-part clamping devices horizontally outwards or inwards in each case on the pressure plate on which they are mounted.

The tablets deemed to be resistant to breaking under a specific load include not only those which have not broken but also those which may have suffered plastic deformation under the action of the force.

In the case of the dosage forms according to the invention, breaking strength is determined in accordance with the stated method, dosage forms other than tablets also being tested.

The following Examples illustrate the invention purely by way of example and without restricting the general concept of the invention.

EXAMPLES

Example 1

| Components | Per tablet | Per batch |
| --- | --- | --- |
| Tramadol HCl | 100.0 mg | 1495.0 g |
| Polyethylene oxide, NF, MW 7 000 000 (Polyox WSR 303, Dow Chemicals) | 167.8 mg | 2508.6 g |
| Hydroxypropylmethylcellulose 100 000 mPa · s | 33.5 mg | 500.8 g |
| Polyethylene glycol (PEG 6000) | 33.5 mg | 500.8 g |
| Butylhydroxytoluene (BHT) | 0.2 mg | 3.0 g |
| Total weight | 335.0 mg | 5008.2 g |

The stated quantity of BHT was dissolved in ethanol (96%), such that a 7.7% (mass/mass) ethanolic solution was obtained. This was mixed initially with 150 g of polyethylene oxide in a high speed mixer for 30 minutes and then the remaining quantity of polyethylene oxide was added and stirring continued for a further 30 minutes. The composition was dried for 12 h at 40° C.

All the further components were added and mixed for 15 min in a free-fall mixer. The powder mixture was apportioned into an extruder. Extrusion was performed using a model Micro 27 GL 40 D double screw extruder with a spindle diameter of 18 mm manufactured by Leistritz (Nürnberg). Screws with blunt ends were used, the hex socket at the end of the screws being closed with a cap. The die used is a heatable round die with a diameter of 8 mm. The entire process was performed under an $N_2$ atmosphere.

The following parameters were selected for extrusion:
Screw speed: 100 rpm
Throughput: 4 kg/h
Product temperature: 125° C.
Casing temperature: 120° C.

The extrudate, which was still hot, was cooled under a nitrogen atmosphere. The cooled strand was singulated into biplanar tablets. The tablets did not break when exposed to a force of 500 N. The tablets could not be comminuted either with a hammer or with the assistance of a mortar and pestle.

The colour of the cooled strand or of the 10 tablets singulated therefrom was determined at N 9.5 using the Munsell Book of Colour, such that the dosage form produced by the process according to the invention did not exhibit any discoloration due to the thermoforming with the assistance of an extruder.

The invention claimed is:

1. An abuse-proofed dosage form thermoformed by extrusion without discoloration and having a breaking strength of at least 500 N, which contains a mixture of:
   i) one or more active ingredients with abuse potential (A) selected from the group consisting of opioids,
   ii) optionally physiologically acceptable auxiliary substances (B),
   iii) from 30% by weight to 99.9% by weight of at least one polyalkylene oxide (C), having a molecular weight of from about 4,000,000 g/mol up to 15,000,000 g/mol,
   iv) optionally at least one wax (D), and v) a further material selected from the group consisting of hydroxypropylmethylcellulose, hydroxypropylcellulose and hydroxymethylcellulose, wherein said extrusion takes place in an extruder at a temperature of from at least the softening point of the polyalkylene oxide up to a temperature of below 180° C., and wherein component (C) and/or the optionally present component (D) serve as a controlled release matrix material in which the active ingredient with abuse potential (A) is embedded and said dosage form not being in multiparticulate form.

2. The dosage form according to claim 1, which is in the form of a tablet.

3. The dosage form according to claim 1, wherein said polyalkylene oxide is polyethylene oxide, polymethylene oxide, polypropylene oxide, a copolymer thereof or a mixture thereof.

4. The dosage form according to claim 1, which contains as the wax (D) at least one natural, semi-synthetic or synthetic wax with a softening point of at least 60° C.

5. The dosage form according to claim 4, wherein the wax (D) is carnauba wax or beeswax.

6. The dosage form according to claim 1, which additionally comprises at least one of the following components a)-f):
 (a) at least one substance which irritates the nasal passages and/or pharynx,
 (b) at least one viscosity-increasing agent, which, with the assistance of a necessary minimum quantity of an aqueous liquid, forms a gel with the extract obtained from the dosage form,
 (c) at least one antagonist for the active ingredient or active ingredients with abuse potential,
 (d) at least one emetic,
 (e) at least one dye as an aversive agent, and
 (f) at least one bitter substance.

7. The dosage form according to claim 6, wherein the component (a) irritant substance causes burning, itching, an urge to sneeze, increased formation of secretions or a combination of at least two of these stimuli.

8. The dosage form according to claim 6, wherein the component (a) irritant substance is based on one or more constituents of at least one hot substance drug.

9. The dosage form according to claim 8, wherein the hot substance drug is at least one drug selected from the group consisting of *Allii sativi bulbus* (garlic), *Asari rhizoma cum herba* (Asarum root and leaves), *Calami rhizoma* (calamus root), *Capsici fructus* (capsicum), *Capsici fructus acer* (cayenne pepper), *Curcumae longae rhizoma* (turmeric root), *Curcumae xanthorrhizae rhizoma* (Javanese turmeric root), *Galangae rhizoma* (galangal root), *Myristicae semen* (nutmeg), *Piperis nigri fructus* (pepper), *Sinapis albae semen* (white mustard seed), *Sinapis nigri semen* (black mustard seed), *Zedoariae rhizoma* (zedoary root) and *Zingiberis rhizoma* (ginger root).

10. The dosage form according to claim 8, wherein the constituent of the hot substance drug is an o-methoxy(methyl)phenol compound, an acid amide compound, a mustard oil or a sulfide compound or is derived from such a compound.

11. The dosage form according to claim 8, wherein the constituent of the hot substance drug is at least one constituent selected from the group consisting of myristicin, elemicin, isoeugenol, β-asarone, safrole, gingerols, xanthorrhizol, capsaicinoids, piperine, glucosinolates, and a compound derived from these constituents.

12. The dosage form according to claim 6, wherein component (b) is at least one viscosity-increasing agent selected from the group consisting of microcrystalline cellulose with 11 wt. % carboxymethylcellulose sodium, carboxymethylcellulose sodium, polyacrylic acid, locust bean flour, pectins from citrus fruit or apples, waxy maize starch, sodium alginate, guar flour, iota carrageen, karaya gum, gellan gum, galactomannan, tara bean flour, propylene glycol alginate, apple pectin, sodium hyaluronate, tragacanth, tara gum, fermented polysaccharide welan gum, xanthan gum.

13. The dosage form according to claim 6, wherein component (c) is at least one opioid antagonist selected from the group consisting of naloxone, naltrexone, nalmefene, nalid, nalmexone, nalorphine, naluphine and a corresponding physiologically acceptable compound.

14. The dosage form according to claim 6, wherein the component (c) used is at least one neuroleptic as a stimulant antagonist.

15. The dosage form according to claim 6, wherein the component (d) emetic is based on one or more constituents of ipecacuanha (ipecac) root, and/or is apomorphine.

16. The dosage form according to claim 6, wherein component (e) is at least one physiologically acceptable dye.

17. The dosage form according to claim 6, wherein component (f) is at least one bitter substance selected from the group consisting of aromatic oils, fruit aroma substances, and mixtures thereof comprising at least 2 components, denatonium benzoate and mixtures thereof comprising at least 2 components.

18. The dosage form according to claim 6, wherein the active ingredient or active ingredients (A) is/are spatially separated from component (c) and/or (d) and/or (f), wherein the active ingredient or active ingredients (A) is/are present in at least one subunit (X) and components (c) and/or (d) and/or (f) is/are present in at least one subunit (Y), and, when the dosage form is correctly administered, components (c) and/or (d) and/or (f) from subunit (Y) do not exert their effect in the body and/or on taking 19. A process for the production of a dosage form according to claim 1, said process comprising:
 i) mixing one or more active ingredients with abuse potential selected from the group consisting of opioids with 30% to 99.9% by weight of a polyalkylene oxide having a molecular weight of from about 4,000,000 g/mol up to 15,000,000 g/mol and a further material selected from the group consisting of hydroxypropylmethylcellulose, hydroxypropylcellulose and hydroxymethylcellulose to form one or more resultant mixtures,
 ii) heating the resultant mixture or the resultant mixtures in the extruder to a temperature of from at least the softening point of the polyalkylene oxide up to a temperature below 180° C. and extruding an extrudate through the outlet orifice of the extruder by application of sufficient force to apply a pressure of at least 10 bar to the mixture or mixtures immediately before emerging from the outlet orifice,
 iii) singulating and forming the still plastic extrudate into the dosage form, or
 iv) forming cooled and optionally reheated singulated extrudate into the dosage form,
 wherein process steps ii) and iii) and optionally process steps i) and iv) are performed under an inert gas atmosphere.

20. The process according to claim 19, wherein mixing of the components i) also proceeds in the extruder under an inert gas atmosphere.

21. The process according to claim 19, wherein the mixtures according to i) are coextruded or separately extruded.

22. The process according to claim 19, wherein the mixture or the mixtures according to i) are extruded through a die with at least one bore.

23. The process according to claim 19, wherein the extrudate is singulated by chopping.

24. The process according to claim 19, wherein the extrudate is in the form of a strand and is shaped and singulated with the assistance of contrarotating calender rolls comprising opposing recesses in their outer sleeve.

25. The process according to claim 19, wherein the singulatable extrudate is pelletised or pressed into tablets.

26. The process according to claim 19, wherein nitrogen is used as the inert gas atmosphere.

27. The dosage form according to claim 1, which is obtainable by a process according to claim 19.

28. The dosage form of claim 1, wherein said extrusion is conducted at a temperature ranging from the softening point of said polyalkylene oxide up to a temperature below 180° C. and under conditions which exert a pressure of at least 10 bar on the dosage form composition immediately before emerging from the outlet of the extruder.

29. The process of claim 19, wherein the extrudate is cooled and singulated into singulated extrudates.

30. The process of claim 29, wherein said singulated extrudates are press-molded into tablets.

31. The dosage form of claim 1, wherein said opioid (A) is selected from the group consisting of (1R,2R)-3-(3-dimethylamino-1-ethyl-2-methyl-propyl)-phenol, oxycodone, oxymorphone, hydromorphone and morphine, the physiologically acceptable esters thereof and the physiologically acceptable salts thereof.

* * * * *